United States Patent
Yarmush et al.

(10) Patent No.: US 12,426,850 B2
(45) Date of Patent: Sep. 30, 2025

(54) ULTRASOUND-GUIDED ALIGNMENT AND INSERTION OF PERCUTANEOUS CANNULATING INSTRUMENTS

(71) Applicant: Rutgers, The State University of New Jersey, New Brunswick, NJ (US)

(72) Inventors: Martin L. Yarmush, Newton, MA (US); Alvin Chen, Cambridge, MA (US); Max Balter, Boston, MA (US); Joshua Leipheimer, Highland Park, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 18/586,675

(22) Filed: Feb. 26, 2024

(65) Prior Publication Data

US 2024/0188927 A1   Jun. 13, 2024

Related U.S. Application Data

(62) Division of application No. 17/284,018, filed as application No. PCT/US2019/055386 on Oct. 9, 2019, now Pat. No. 11,992,362.

(Continued)

(51) Int. Cl.
*A61B 8/08* (2006.01)
*A61B 8/00* (2006.01)
(Continued)

(52) U.S. Cl.
CPC ............. *A61B 8/0841* (2013.01); *A61B 8/06* (2013.01); *A61B 8/12* (2013.01); *A61B 8/4218* (2013.01);
(Continued)

(58) Field of Classification Search
CPC ........... A61B 8/0841; A61B 8/06; A61B 8/12; A61B 8/466; A61B 2562/0219
See application file for complete search history.

(56) References Cited

U.S. PATENT DOCUMENTS 5,459,570 A     10/1995   Swanson et al.
10,029,037 B2   7/2018    Muller et al.
(Continued)

FOREIGN PATENT DOCUMENTS

DE   10-2017-201439 A1   8/2018
JP   2012-035010 A       2/2012
(Continued)

OTHER PUBLICATIONS

Balter ML, Chen AI, Maguire TJ, Yarmush ML. Adaptive kinematic control of a robotic venipuncture device based on stereo vision, ultrasound, and force guidance. IEEE Transactions on Industrial Electronics. Apr. 21, 2016;64(2):1626-35.

(Continued)

*Primary Examiner* — Rochelle D Turchen
(74) *Attorney, Agent, or Firm* — Lerner David LLP

(57) ABSTRACT

A device and method for directing a cannula toward a target location under a patient's skin. The device is handheld and the device operations may be automated. The device includes an imaging probe for imaging the target location, a positioning unit for manipulating a cannula towards the target location, and a processor. The processor receives imaging data from the imaging probe, cannula pose data from at least one cannula position sensor, and device pose data from at least one device position sensor. The target location is identified from the imaging data, and a trajectory for manipulating the cannula towards the target location is determined based on the imaging data, the cannula pose data, and the device pose data. The processor may determine that the trajectory becomes misaligned with the target posi- (Continued)

tion, and may update to a corrected trajectory based on the imaging data, cannula pose data, and device pose data.

21 Claims, 19 Drawing Sheets

Related U.S. Application Data

(60) Provisional application No. 62/743,283, filed on Oct. 9, 2018.

(51) Int. Cl.
  *A61B 8/06* (2006.01)
  *A61B 8/12* (2006.01)
  *A61B 34/20* (2016.01)

(52) U.S. Cl.
  CPC ...... *A61B 8/466* (2013.01); *A61B 2034/2065* (2016.02); *A61B 2562/0219* (2013.01)

(56) References Cited

U.S. PATENT DOCUMENTS

| | | |
|---|---|---|
| 2010/0010505 A1 | 1/2010 | Herlihy et al. |
| 2010/0152761 A1* | 6/2010 | Mark ............ A61B 17/320758 606/180 |
| 2012/0108971 A1 | 5/2012 | Miyama et al. |
| 2012/0190981 A1 | 7/2012 | Harris et al. |
| 2014/0343416 A1 | 11/2014 | Panescu et al. |
| 2016/0113724 A1 | 4/2016 | Stolka et al. |
| 2017/0014194 A1 | 1/2017 | Duindam et al. |
| 2017/0055940 A1 | 3/2017 | Shoham |
| 2017/0273712 A1 | 9/2017 | Carlson et al. |
| 2019/0336674 A1 | 11/2019 | Schermeier et al. |
| 2020/0060772 A1 | 2/2020 | Konh et al. |

FOREIGN PATENT DOCUMENTS

| | | |
|---|---|---|
| JP | 2012-090820 A | 5/2012 |
| JP | 2014-239831 A | 12/2014 |
| WO | 2006/123282 A1 | 11/2006 |
| WO | 2012/088471 A1 | 6/2012 |
| WO | 2015/031481 A1 | 3/2015 |
| WO | 2015/179505 A1 | 11/2015 |

OTHER PUBLICATIONS

Chen AI, Balter ML, Maguire TJ, Yarmush ML. 3D near infrared and ultrasound imaging of peripheral blood vessels for real-time localization and needle guidance. InInternational Conference on Medical Image Computing and Computer-Assisted Intervention Oct. 17, 2016 (pp. 388-396). Springer, Cham.

International Search Report including Written Opinion for PCT/US19/55386 mailed May 20, 2020; 53 pages.

Balter Max L et al: "Adaptive Kinematic Control of a Robotic Venipuncture Device Based on Stereo Vision, Ultrasound, and Force Guidance," IEEE Transactions on Industrial Electronic, IEEE Service Center, Piscataway, NJ, USA, vol. 64, No. 2, Feb. 1, 2017 (Feb. 1, 2017), pp. 1626-1635, XP011638652, ISSN: 0278-0046, DOI: 10.1109/TIE.2016.2557306 [retrieved on Jan. 10, 2017] * abstract; figures, 1, 2, 3 *.

Supplementary European Search Report issued in EP Appln. No 19872078.8 mailed Jun. 2, 2022 (9 pages).

Extended European Search Report including Search Opinion from EP Appl. No. 24191907.5, dated Oct. 22, 2024, pp. 1-8.

* cited by examiner

Needle into vessel lumen center

Needle overshoot through posterior wall

Needle against anterior vessel wall

Needle slips along vessel lateral wall

FIGURE 10F
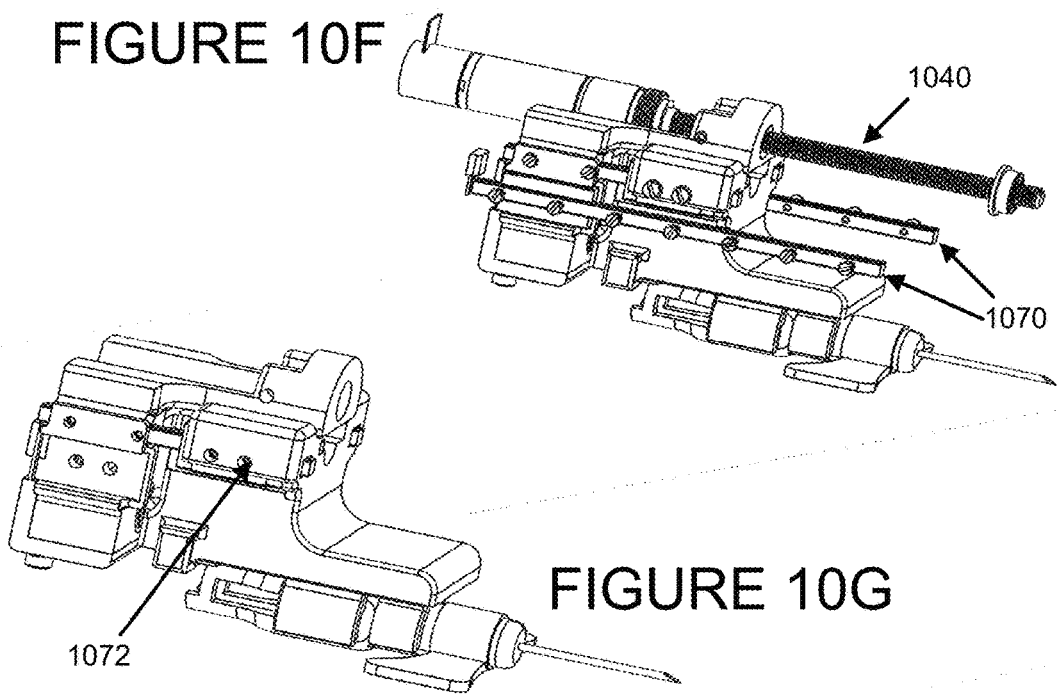
FIGURE 10G
FIGURE 10H
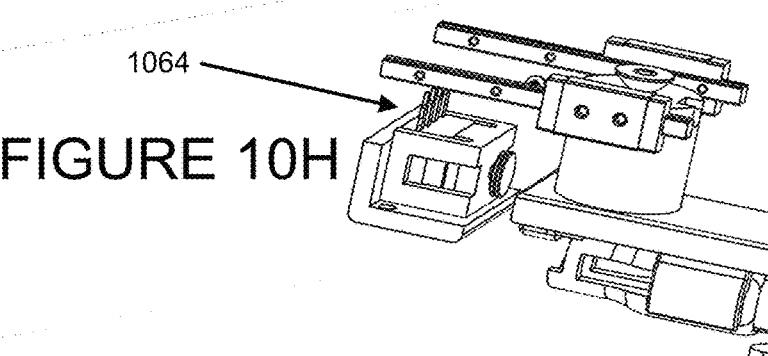
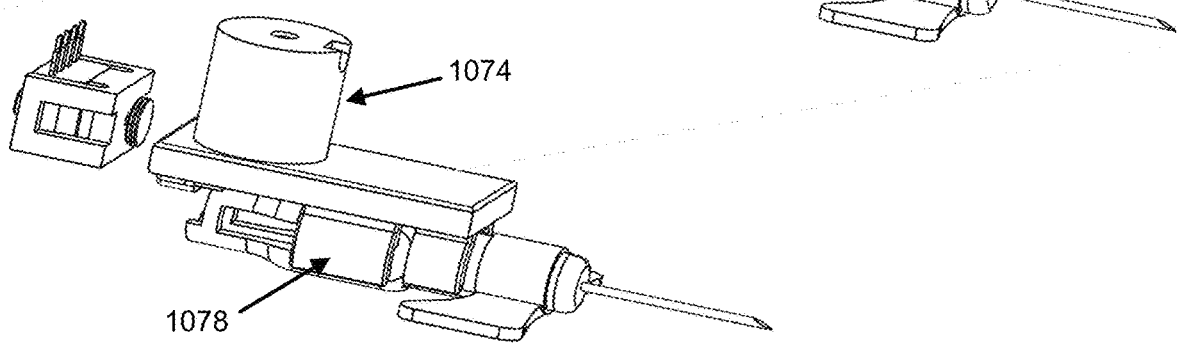
FIGURE 10I

ULTRASOUND-GUIDED ALIGNMENT AND INSERTION OF PERCUTANEOUS CANNULATING INSTRUMENTS

CROSS-REFERENCE TO RELATED APPLICATIONS

The present application is a divisional application of U.S. application Ser. No. 17/284,018, filed Oct. 9, 2019, which is a national phase entry under 35 U.S.C. § 371 of International Application No. PCT/US2019/055386 filed Oct. 9, 2019, published in English, which claims priority from U.S. Provisional Patent Application No. 62/743,283 filed Oct. 9, 2018, all of which are incorporated herein by reference.

STATEMENT REGARDING FEDERALLY SPONSORED RESEARCH OR DEVELOPMENT

This invention was made with government support under Agreement No. R01EB020036 awarded by the National Institutes of Health. Agreement No. EB018191 awarded by the National Institutes of Health. Agreement No. T32 GM008339 awarded by the National Institutes of Health. Agreement No. DGE-0937373 awarded by the National Science Foundation, and Agreement No. P200A150131 awarded by the Department of Education. Therefore, the government may have certain rights in the invention.

BACKGROUND OF THE INVENTION

The process of venipuncture, inserting a cannula into a vein such as to withdraw a blood sample or deliver intravenous (IV) fluid, is one of the most ubiquitous clinical routines practiced in medicine. Oftentimes it can be challenging to find a suitable venipuncture site, particularly in patients with dark skin or a high body mass index. Even after a target vein is identified, the process of inserting the cannula into the vessel can also be difficult. Failed insertion attempts frequently occur. Sometimes, the failure may be caused by unexpected movement of the vein, such as from pressure applied by the needle tip to the vein causing the vein to deform, move, or roll. Other times, the failure may be caused by unexpected movement of the patient or by the clinician holding the cannulating instrument. Poorly introduced needles may result in complications such as increased pain, internal bleeding, or leakage of IV fluids into the extravascular tissue.

Various imaging technologies based on near-infrared (NIR) light or ultrasound (US) have been introduced to aid clinicians in visualizing veins. However, studies have indicated that these imaging technologies on their own do not improve first-stick success rates significantly compared to manual techniques. In order to improve the rate of venipuncture insertion accuracy, devices have been developed to combine the NIR and US imaging techniques with an automated robotic system that guides the cannula to the center of the vessel based on the image data.

FIG. 1 is a side profile view of an example prior art automated cannulation system 100. The automated cannulation system 100 includes a positioning unit 110 attached to an ultrasound imaging unit 120. The positioning unit 110 may include a robotic arm 112 configured to control the positioning of a cannula 115, such as a needle, and may include multiple degrees of freedom for manipulating the cannula 115. The ultrasound imaging unit 120 may further include a probe 122 attached to an end of the unit 120, whereby the unit 120 is configured to acquire an US image of a portion of the patient (not shown) positioned opposite the probe 122. The probe 122 may be made from a flexible material designed to flex and conform to the imaged portion of the patient (e.g., the patient's arm). In some examples, the probe 122 may further include a gel compartment 125 configured to contain ultrasound gel for improving acquisition of the US image.

In FIG. 2, the prior art automated cannulation system 100 is being used to insert a needle into a patient's arm 201. The patient's arm 201 may be positioned on a platform 210 to ensure the patient's comfort and stability of the arm 201. The cannula 115 may be positioned at an angle above the patient's arm 201, such that a tip of the cannula 115 is positioned to engage a cannulation site 225 directly below the imaging probe 122.

FIG. 3 is a side profile view of an example prior art positioning unit 110 having four degrees of freedom. The positioning unit 110 includes a robotic arm 112 having a base 302, a first extension member 304 extending from the base 302, a second extension member 306 connected to and extending from the first extension member 304, and a cannulating instrument receptacle 308 for receiving the cannula 115. The positioning unit 110 in FIG. 3 has four degrees of freedom: (1) rotating the base 302 in the xy-plane around focal point 312; (2) rotating the first extension member 304 in the xz-plane (technically, the plane formed by the z-axis and the particular axis of the first extension member) around focal point 314; (3) rotating the second extension member 306 in the xz-plane (technically, the plane formed by the z-axis and the particular axis of the second extension member) around focal point 316; and (4) translating the cannula 115 forward or backward along its axis 318.

The imaging technologies in the example automated device and other known devices are capable of tracking a patient's movement, including movement of the patient's target location (e.g., a vein underneath the patient's skin). These devices are further capable of adjusting the trajectory for accurate insertion into the target location. However, in order for a device to provide such accurate tracking and repositioning, it must be affixed to a benchtop or other stationary platform, as shown in FIG. 2. The benchtop provides necessary stability in order to ensure that the cannulating instrument does not unexpectedly move, but rather only moves as guided by the positioning unit.

This need for a venipuncture device to be fixed into place before use is a disadvantage. First of all, not every clinical setting includes a benchtop or other platform from which the device may be mounted. Besides, it may take a clinician significant time to mount and dismount the device. Ultimately, while the automated venipuncture devices provide some advantages over the prior handheld methods of venipuncture, such as in terms of accuracy, some clinicians may find the automated devices inconvenient, and some clinical settings may not even be suitable for use of the automated devices.

BRIEF SUMMARY OF THE INVENTION

The present disclosure is directed to a handheld automated cannulation device. The device has the convenience and portability that comes with being handheld, while at the same time providing the improved accuracy associated with other automated devices. In order for the automated device to be used in a handheld fashion, it was necessary to design a control scheme that could quickly and efficiently respond to real-time sensor data while not having to rely on a fixed frame of reference external to the device itself.

One aspect of the disclosure is directed to a device for directing a cannula toward a target location under a patient's skin. The device may include an imaging probe for continuously generating imaging data of the target location, a positioning unit, and a processor. The positioning unit may include a plurality of motors configured to manipulate a cannula attached to the positioning unit. The positioning unit may further include at least one cannula position sensor configured to generate cannula pose data indicating a position and orientation of the cannula based on movement of the motors. The positioning unit may further include at least one device position sensor configured to generate device pose data indicating an orientation and position of the device.

The processor may be configured to receive imaging data from the imaging probe, receive cannula pose data from the at least one cannula position sensor, receive device pose data from the at least one device position sensor, identify the target location from the imaging data, and determine a trajectory for manipulating the cannula towards the target pose based on the imaging data, the cannula pose data, and the device pose data. The processor may further be configured to instruct the positioning unit to manipulate the cannula according to the determined trajectory. The processor may also be configured to identify the determined trajectory becoming misaligned with the target position, to update the determined trajectory to a corrected trajectory based on the imaging data, the cannula pose data, and the device pose data, and to instruct the positioning unit to manipulate the cannula according to the corrected trajectory.

In some examples, the imaging probe may be an ultrasound probe. The imaging data generated by the imaging probe may be any one of two-dimensional imaging data, volumetric three-dimensional imaging data, or biplanar imaging data. In some examples, the processor may be further configured to identify and determine a pose of a target vessel under the patient's skin based on the imaging data. In some examples, the device may be adapted to obtain imaging data of the target location from a plurality of angles. The processor may be further configured to construct three-dimensional imaging data from the received imaging data obtained from the plurality of angles, to determine the three-dimensional pose of the target location under the patient's skin from the imaging data obtained from the plurality of angles, or both.

In some examples, the imaging data may include video data of the target location obtained at different times, and the processor may be configured to determine the trajectory for manipulating the cannula towards the target pose based on a comparison between previous and subsequent frames of the video data In some examples, the positioning unit may be configured to manipulate the cannula in at least two degrees of freedom.

In some examples, the processor may be configured to identify the determined trajectory becoming misaligned with the target position based on device pose data received from the at least one device position sensor, such as a camera, an electromagnetic sensor, a gyroscope, an accelerometer, or any combination of the above.

In some examples, the device may include a force sensor configured to generate force data indicating a measured amount of force exerted on the cannula. The processor may be configured to receive the force data from the force sensor, update the cannula pose data to a corrected position and orientation based on the received force data, and instruct the cannula positioning unit to manipulate the cannula according to the corrected position and orientation. Additionally or alternatively, the processor may be configured to receive the force data from the force sensor, obtain a force profile from the force data, and classify the obtained force. Examples of force classifications include successful cannulation events, vessel rolling events, undershoot events, and overshoot events. The processor may be able to classify the force data into one or more of these categories. Further, in some examples, in an absence of a successful cannulation event, the processor may be configured to instruct the positioning unit to manipulate the cannula in response to the classified event.

In some examples, the device may further include a blood flash sensor configured to generate blood flash data indicating a flow of blood into the cannula. The processor may be configure to receive the blood flash data from the blood flash sensor, and instruct the cannula positioning unit to manipulate the cannula based further on the blood flash data.

In some examples, each motor may be associated with a corresponding motor sensor. The motor sensors may be configured to generate cannula pose data indicating a position and orientation of the cannula based on movement of the corresponding motors.

Another aspect of the disclosure is directed to a method of directing a cannula toward a target location under a patient's skin. The method may be executed by a processor coupled to an imaging probe for continuously generating imaging data of the target location, and to a positioning unit including a plurality of motors configured to manipulate a cannula attached to the positioning unit, each motor being associated with at least one cannula position sensor configured to generate cannula pose data indicating a position and orientation of the cannula based on movement of the corresponding motors. The positioning unit may further include at least one device position sensor configured to generate device pose data indicating an orientation and position of the device. The method may involve: receiving imaging data from the imaging probe; receiving cannula pose data from the at least one cannula position sensor; receiving device pose data from the at least one device position sensor; identifying the target location from the imaging data; determining a trajectory for manipulating the cannula towards the target pose based on the imaging data, the cannula pose data, and the device pose data; instructing the positioning unit to manipulate the cannula according to the determined trajectory; identifying the determined trajectory becoming misaligned with the target position; updating the determined trajectory to a corrected trajectory based on the imaging data, the cannula pose data, and the device pose data; and instructing the positioning unit to manipulate the cannula according to the corrected trajectory.

In some examples, the method may further involve identifying and determining a pose of a target vessel under the patient's skin based on the imaging data, and instructing the positioning unit to manipulate the cannula based on the determined pose of the target vessel.

In some examples, receiving imaging data from the probe may involve receiving imaging data from a plurality of angles, and the method may further involve constructing three-dimensional imaging data from the received imaging data obtained from the plurality of angles. In some examples, the method may involve determining the pose of the target location under the patient's skin from the imaging data obtained from the plurality of angles.

In some examples, instructing the positioning unit to manipulate the cannula may involve providing instructions for manipulating each of the positioning unit's two or more degrees of freedom. In some examples, identifying the determined trajectory becoming misaligned with the target location may be based on the device pose data received from the device position sensor.

In some examples, determining the cannula pose data may be based on the imaging data using at least one of a computer vision algorithm or an electromagnetic sensor.

In some examples, the processor may be coupled to a force sensor for generating force data indicating a measured amount of force exerted on the cannula. The method may further involve receiving the force data from the force sensor, updating the cannula positioning data to a corrected position and orientation based on the received force data, and instructing the cannula positioning unit to manipulate the cannula according to the corrected position and orientation. Additionally or alternatively, the method may further involve obtaining a force profile from the force data, and classifying the obtained force profile (e.g., a successful cannulation event, vessel rolling event, undershoot event, overshoot event). Further, in some instances, in an absence of a successful cannulation event, the method may involve instructing the positioning unit to manipulate the cannula in response to the classified event.

Yet another aspect of the disclosure is directed to a device for inserting a needle into a blood vessel of a patient. The device may include an ultrasound probe configured to image a portion of the blood vessel positioned within a field-of-view of the ultrasound probe, a mechanical arm affixed to the ultrasound probe, and a processor for controlling operation of the one or more motors included in the mechanical arm. The needle may be attachable to the mechanical arm. The mechanical arm may include one or more motors configured to manipulate a position and orientation of the needle. The processor may be configured to define a frame of reference for controlling the one or more motors based on spatial parameters of the blood vessel. The mechanical arm may be adapted to enable insertion of the needle into the portion of the blood vessel positioned within a field-of-view of the ultrasound probe at an angle. The processor controlling operation of the one or more motors may be automated based at least in part on the image data from the ultrasound probe, and the device may be configured to be hand-held.

In some examples, the motors of the mechanical arm may be configured to manipulate at least a depth of insertion of the needle and an angle of insertion of the needle. The processor may be communicatively coupled to the probe, and may be configured to determine the depth of insertion based at least in part from data received from the probe. The angle of insertion may be determined based on the depth of insertion.

In some examples, the device may further include an accelerometer and a gyroscope configured to provide data indicating motion and orientation of the device, respectively, to the processor. The processor may control operation of the one or more motors, and may be automated based in part on the data from the accelerometer and gyroscope.

Yet a further aspect of the present disclosure is directed to a device for directing a cannula toward a target location under a patient's skin. The device may include at least one motor configured to manipulate a cannula in a lengthwise direction of the cannula towards a target, a force sensor configured to generate force data indicating a measured amount of force exerted on the cannula; a blood flash sensor configured to generate blood flash data indicating a flow of blood into the cannula; and a processor configured to receive the force data from the force sensor, receive the blood flash data from the blood flash sensor, determine occurrence of a successful cannulation event based on a combination of the force data and the blood flash data, and upon the occurrence of a successful cannulation event, instruct the at least one motor to cease manipulating the cannula towards the target.

In some examples, the device may further include a cannula position sensor configured to generate cannula pose data indicating a position of the cannula based on movement of the at least one motor. The processor may be configured to determine the successful cannulation event based on a combination of the force data, the blood flash data, and the cannula pose data.

In some examples, the device may further include an imaging probe for obtaining ultrasound imaging data. The processor may be configured to determine a likelihood of failure of the cannulation event based on a combination of the force data, the blood flash data, the ultrasound imaging data, and the cannula pose data, and determine an adjustment to the cannula that reduces the likelihood of failure of the cannulation event based on a combination of the force data, the blood flash data, the ultrasound imaging data, and the cannula pose data.

In some examples, the processor may be configured to obtain a force profile from the received force data, classify the obtained force profile as one of a successful cannulation event or an unsuccessful cannulation event, and upon occurrence of an unsuccessful cannulation event, instruct the one or more motors to manipulate the cannula in a reverse direction.

BRIEF DESCRIPTION OF THE DRAWINGS

FIGS. 10C-10I are perspective views of portions of the cannulation device of FIG. 10A.

DETAILED DESCRIPTION

Figure 4:
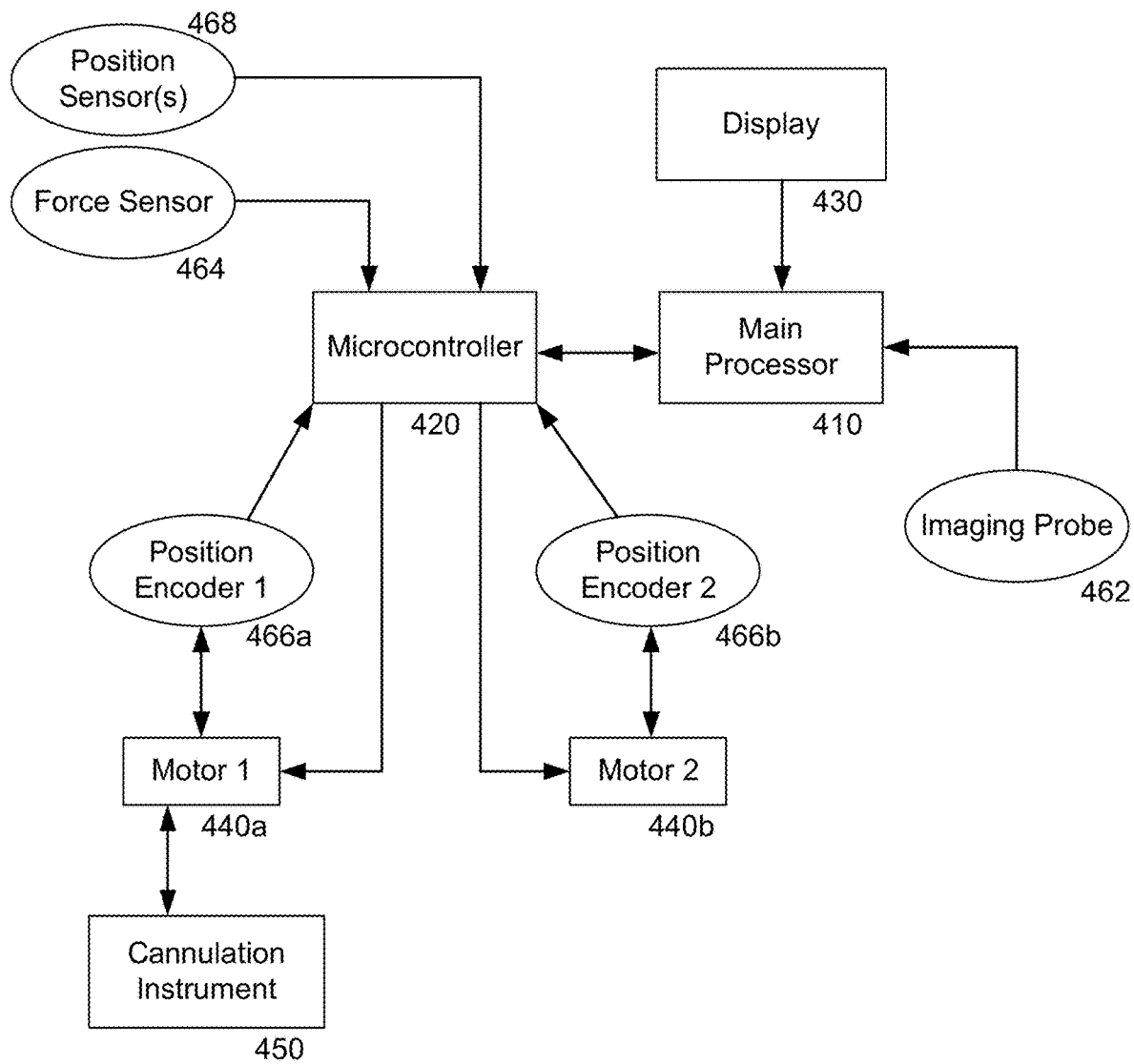
FIG. 4 is a block diagram of a cannulation device in accordance with an aspect of the present disclosure.

FIG. 4 is a block diagram illustrating a control scheme for a handheld cannulation device 400 according to the present disclosure. The cannulation device 400 includes each of a main processor 410, a microcontroller 420, a display 430, and a plurality of motor controllers 440a. 440b for controlling various axes of freedom of a cannulation instrument 450. The main processor 410 may be any processing unit known in the art with sufficient processing power to receive process and output mage data at video frame rates. The microcontroller 420 may be an integrated chip or other processing unit known in the art with sufficient processing capacity to control a robotic arm, including the processing and relaying of sensor inputs and instructions for controlling motor activity.

The microcontroller 420 may be configured to receive either one or a combination of analog and digital inputs from various sensors, to process those inputs, and relay the inputs to the main processor over a controller area network (CAN) connection. In some instances, the main processor 410 may include a different connection, such as a universal serial bus (USB) connection, in which case, the sensor data may be relayed over a CAN-to-USB connection. Conversely, instructions relayed from the main processor 410 through the microcontroller 420 may be provided through a USB-to-CAN connection.

The display 430 may be configured to provide a two-dimensional or three-dimensional image of the cannulation target location and the cannulation instrument. A cannulation trajectory, such as an expected trajectory of the cannulation instrument to reach the target vessel, may be superimposed on the image. The image may be updated or refreshed in real time or at video frame rates. The display may further be configured to allow a clinician to specify a location in an image presented thereon, such as specifying a target location.

The display 430 may further be configured to initialize image processing routines. For instance, automatic segmentation of the boundaries of a vessel may be initialized through the interaction between the user and the device 400 through the display 430. For instance, the ultrasound transducer may be moved around until the target vessel is centered in the ultrasound image (the display may include crosshairs to indicate the image center). Once centered, processing software in the device may be manually started to search for a segmentation starting from the center of the image. After the initial segmentation, the target can be tracked automatically afterwards.

A similar way of initializing automatic segmentation algorithms can be used when the probe is oriented longitudinally. In this scenario, the vessel may be aligned so that the vessel is parallel with the longitudinal image. The segmentation algorithm can then identify the vessel from the longitudinal image and the identified vessel can be automatically tracked.

The center of the blood vessel can be manually or automatically detected based on the ultrasound image. In the case of automatic detection, image segmentation algorithms may be applied for both longitudinal and transverse orientations of the ultrasound probe. In the transverse orientation, where the grayscale B-mode ultrasound image shows a cross-section of the vessel, the algorithm may detect ellipse-like structures in the image, and may initialize coarse segmentation contours for potential vessel structures based on the detected ellipse-like structures. These initial contours may be refined in an iterative manner. In the longitudinal orientation, where the B-mode ultrasound image is parallel with the vessel, the algorithm may instead detect elongated tube-like structures with an expected diameter in the range of 1 to 5 mm, and a similar process of contour initialization and refinement may be performed on the detected tube-like structures.

Additionally, the B-mode image segmentation algorithms may be supplemented with image information extracted from the Color Doppler imaging mode. In Color Doppler mode, velocity (rather than tissue backscatter) is detected by the probe. Since blood demonstrates directional motion and velocity whereas surrounding tissues are mostly static, blood flow can be directly visualized through Color Doppler imaging. The Color Doppler image data may be combined with the B-mode intensity image data in several different ways (masking, contour initialization, weighted sum, etc.) in order to improve the accuracy of the segmentation algorithm.

Once the center coordinate of the vessel is identified, the vessel can be tracked from one frame to the next using image-based tracking algorithms. This allows the device to detect tissue motion in real-time and to adjust the instrument pose accordingly. Tracking the vessel in this manner also reduces the need to perform vessel segmentation from scratch in each frame, thus speeding up the computational time.

The cannulation device 400 further includes a plurality of sensors for providing inputs to the main processor 410 and microcontroller 420. The sensors may include an imaging probe 462, such as an ultrasound probe, a force sensor 464 for sensing forces applied to the motor as it drives the cannulation instrument, respective position encoders 466a, 466b for each motor controller 440a, 440b to monitor manipulation of the needle by the device's motors, and a position sensor 468 for tracking changes in translation and orientation of the cannulation device 400. Since the cannulation device is handheld, the position sensor 468 is necessary to track if the cannulation device is moved from its initial location, either advertently or inadvertently.

The main processor 410 and microprocessor 420 are programmed with software instructions for carrying out the operations and protocols outlined in the present disclosure. For instance, the microprocessor may be programmed to receive analog inputs from each of the force sensor, position encoders, and position sensor, process the received inputs into a format acceptable to the main processor, and then transmit the reformatted input data to the main processor for further processing. For further instance, the main processor may be programmed to receive and process imaging data, such as identifying a target location in the patient and determining a trajectory for guiding the cannulation instrument to the target location. The main processor may further determine and continuously track a relative position of the cannulation instrument to the target location based on the received inputs, and may update the determined trajectory based on changes in the relative position.

The processor may compute relative positions and display these to the operator during the cannulation. For example, the processor may automatically extrapolate a final position of the cannulation instrument tip (e.g., where the tip will be upon insertion) based on the instrument's current pose as the instrument is being maneuvered/aligned. An offset distance between the extrapolated tip position and the target position may also computed. Similarly, an expected trajectory of the instrument (e.g., the course that the instrument tip will take during the insertion) may be continuously extrapolated from the instrument's current pose and may be displayed. The extrapolated position within the ultrasound image may be continuously updated, and the updated position displayed. In some instances, the ultrasound image and extrapolated tip position may be further updated while the insertion is being performed, with the updates being computed continuously. The processor may also update the coordinates of the vessel target, for instance to compensate for motions from the tissue, patient, and ultrasound probe. The updated position of the vessel target would then be directed to the instrument positioning unit in order to adjust the pose and trajectory of the instrument tip, minimize the offset distance between the instrument tip and the vessel target, and ensure constant alignment with the vessel target. In yet another example, a cue may be provided to the user when the extrapolated tip position is aligned exactly with the vessel or other target position in 3D space. This cue would indicate that the cannulation can be carried out. Depending on the clinical situation, it can be envisioned that the cannulation is carried out only when the extrapolated tip position and the target position are aligned to within a preset tolerance of error. Such a mechanism would serve as a safety feature preventing erroneous, inaccurate, or unsafe cannulation attempts.

The imaging probe 462 may be an ultrasound (US) imaging unit, capable of detecting target vessels or tissue under the surface of the patient's skin. The US imaging unit may be capable of collecting US images in real-time or video frame rates (e.g., 30 or 60 frames per second, or faster). For some imaging units, the images may be two dimensional. For other units, the images may be bi-planar. In yet further units, the images may be three-dimensional. Example applications of these imaging types are provided in greater detail below. Preferably, the frequency of the ultrasound probe is in the range of about 6 MHz to about 18 MHZ. However, other frequencies may be used if they are determined to yield a higher image quality. For example, deeper tissue structures may require a lower ultrasound frequency, whereas more superficial structures may warrant a higher frequency.

In some examples, the US imaging unit may additionally acquire any one or combination of Color Doppler, Power Doppler, Spectral Doppler, Tissue Doppler, Vector Doppler, or other modes of ultrasound-based imaging. These imaging techniques may be used to detect the presence and direction of blood flow within vessels, so that a suitable vessel for puncture may be selected. Additionally, or alternatively, the imaging probe 462 may be paired with other secondary imaging units, such as visible light imaging (e.g., a camera); an infrared (IR) or near-infrared (NIR) imager; a multispectral imager; structured light or depth imaging, optical tomography techniques; laser Doppler, and so on. Other imaging techniques, such as photoacoustic or optoacoustic imaging techniques may be employed.

The force sensor 464 may be a material having a property that changes in response to an applied force, such as a piezoelectric material or force-sensitive resistor. The material may be embedded in the cannulation device in contact with the cannulation instrument. In one example of operation, as the cannulation instrument moves along a linear degree-of-freedom to advance the cannula, for instance by sliding along ball bearing sliders, both normal forces and frictional forces may act on the cannulation instrument, causing it to push against the force sensor 464 material. This may generate an analog signal which is then digitized by an analog-to-digital converter such as the microprocessor 420, and relayed to the main processor 410. The processor 410 may use the received signal data to monitor an amount of force applied against the material.

Additionally or alternatively, the force sensor may be a current sensor configured to measure an electrical current running through the windings of a cannulation device motor. The electrical current may increase proportionally to the load on the motor, meaning that the measure of electrical current can be indicative of increased forces exerted on the cannulation instrument, such as during puncture of a target vessel wall. Again, the current measurements may be analog measurements that are converted to digital signals and relayed to the processor 410 for further processing. For instance, a series of current measurements over time may be recorded by the processor and then filtered (e.g., by a first-order low-pass digital filter) to yield an indication of force on the cannulation instrument. Taking the case of a needle insertion force for example, the measured force may be the sum of several forces, including but not limited to kinetic and viscous friction, soft tissue elastic deformation, and cutting through the tissue.

Different types of position encoders 466a, 466b may be employed depending on the type of degree of freedom controlled by each encoder's respective motor. For example, if a motor controls a rotational degree of freedom of the positioning unit, then the associated encoder may be a rotary encoder or potentiometer. For further example, if a motor controls a linear degree of freedom of the positioning unit, then the associated encoder may be a linear encoder for interpreting linear translation. Either relative or absolute encoders may be used.

The position sensor 468 may include one or both of a gyroscope and an accelerometer to track motion and tilting of the cannulation device. In one example, the gyroscope may be responsible for tracking an orientation of the device, while the accelerometer is responsible for tracking an overall movement of the device. Other combinations of sensors, such as multiple gyroscopes or multiple accelerometers, may be utilized to yield similar results. In some instances, an inertial measurement unit may be used to track motion. In other instances, stereo cameras may be used in order to improve tracking. Additionally or alternatively, an electromagnetic tracking device may be used to monitor movement of the device. Additionally, or alternatively, image data (e.g., camera image frames, ultrasound image frames) may be used to the track the device at it translates or tilts. In such a case, the images may be processed using a computer vision program, such that changes in the image frames may indicate a shift or tilt in the device.

The position sensor(s) 468 may be utilized for several purposes. One example use of the motion sensor is to form a 3D image from 2D probe imaging data. If the cannulation device includes a 2D imaging probe, such as a two-dimensional ultrasound imaging unit, the device may be swept around the target location of the patient. In this manner, images of the target location can be acquired from multiple angles. The images may be provided to the main processor, and then effectively stitched together to yield a composite 3D image. The use of 3D images for tracking a target vessel, as compared to 2D images, is advantageous for the reasons described further below.

Another example use of the position sensor(s) 468 is to provide a gravity vector. The gravity vector may be overlaid with the probe imaging data in order to help interpret the imaging results. In some instances, this may be useful to help identify the patient's anatomy.

Placement of the position sensor(s) 468 in a particular region of the cannulation device 400 does not limit the sensor's ability to track motion of components in other regions of the device. For instance, if the position sensor is a gyroscope and accelerometer mounted to the imaging probe, it can be used to directly measure probe pose and acceleration. The directly monitored data can then be processed by the main processor to indirectly calculate a pose and a change of displacement of the cannulation instrument based on changes in rotational pose and displacement of the probe, in addition to the known kinematic pose of the cannulation instrument with respect to the probe. In a similar vein, a gyroscope and accelerometer mounted to the cannulation instrument may be used to indirectly calculate a pose and displacement of the imaging probe.

In other examples, each of the probe and cannulation instrument may include its own position sensor. Furthermore, the measurements from the position sensors may be compared to one another in order to check for agreement, provide an added degree of accuracy to the measurements, or both.

Because the cannulation device 400 is handheld and includes the imaging probe, it should be appreciated that the image data received at the main processor is not taken from a fixed position or angle. Therefore, the objects and locations identified in the image data cannot be characterized using an absolute world coordinate system. Instead, a dynamic reference coordinate system must be used to relate the image to the relative position of the cannulation instrument. Since the cannulation instrument and imaging probe are connected to one another, moving the cannulation device will cause each of the cannulation instrument and imaging probe to move in a predictable coordinated fashion.

One challenge that arises from using a handheld cannulation device is the need to define a pose of the cannulation instrument relative to the device and the imaging probe. Because the cannulation device is handheld and liable to be moved or tilted, a fixed coordinate system cannot be used. Instead, the cannulation instrument's pose may be based on one or more sensors that may track movement of the cannulation instrument with respect to the device.

Figure 1:
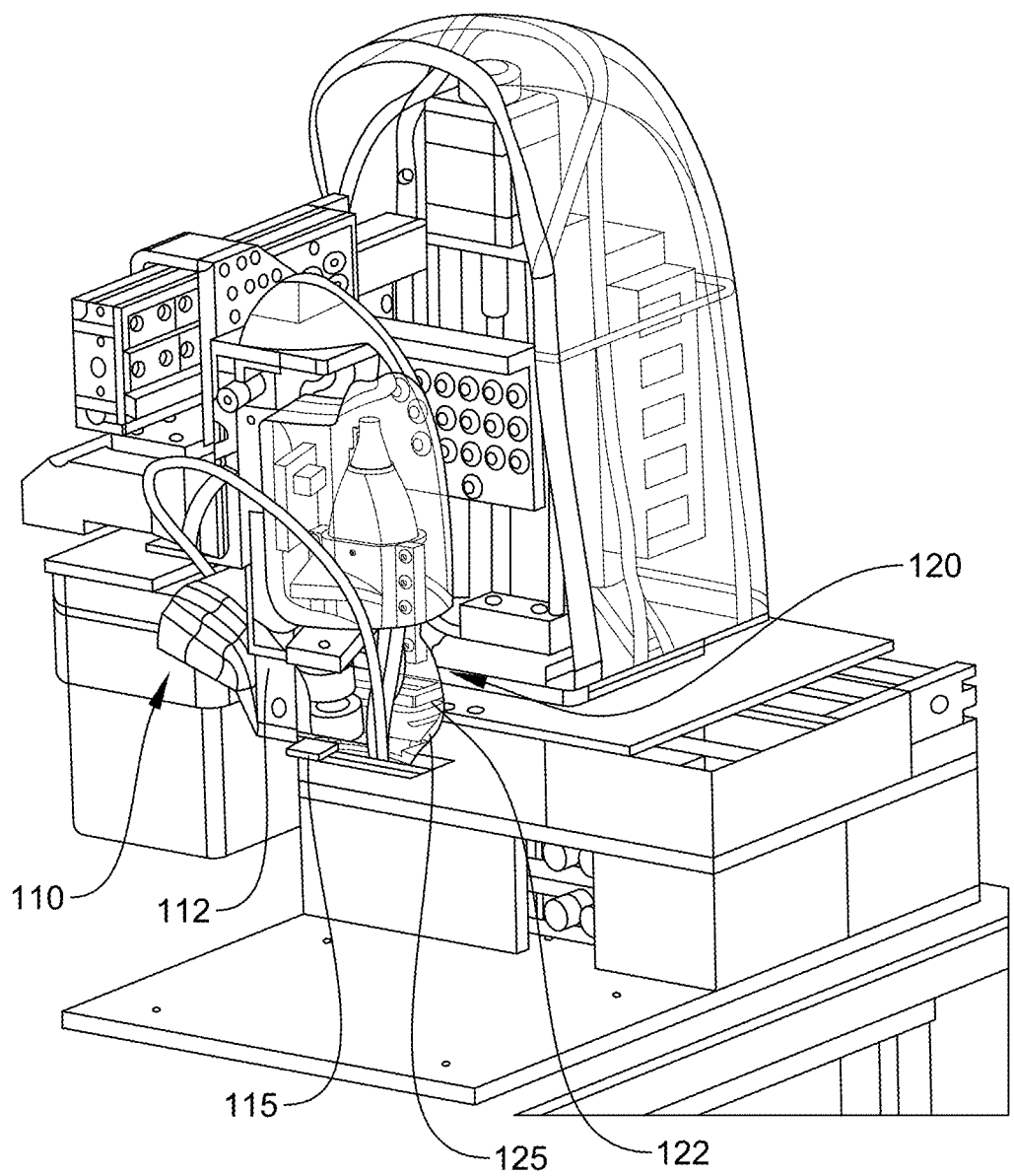
FIG. 1 is a prior art automated cannulation device.
Figure 2:
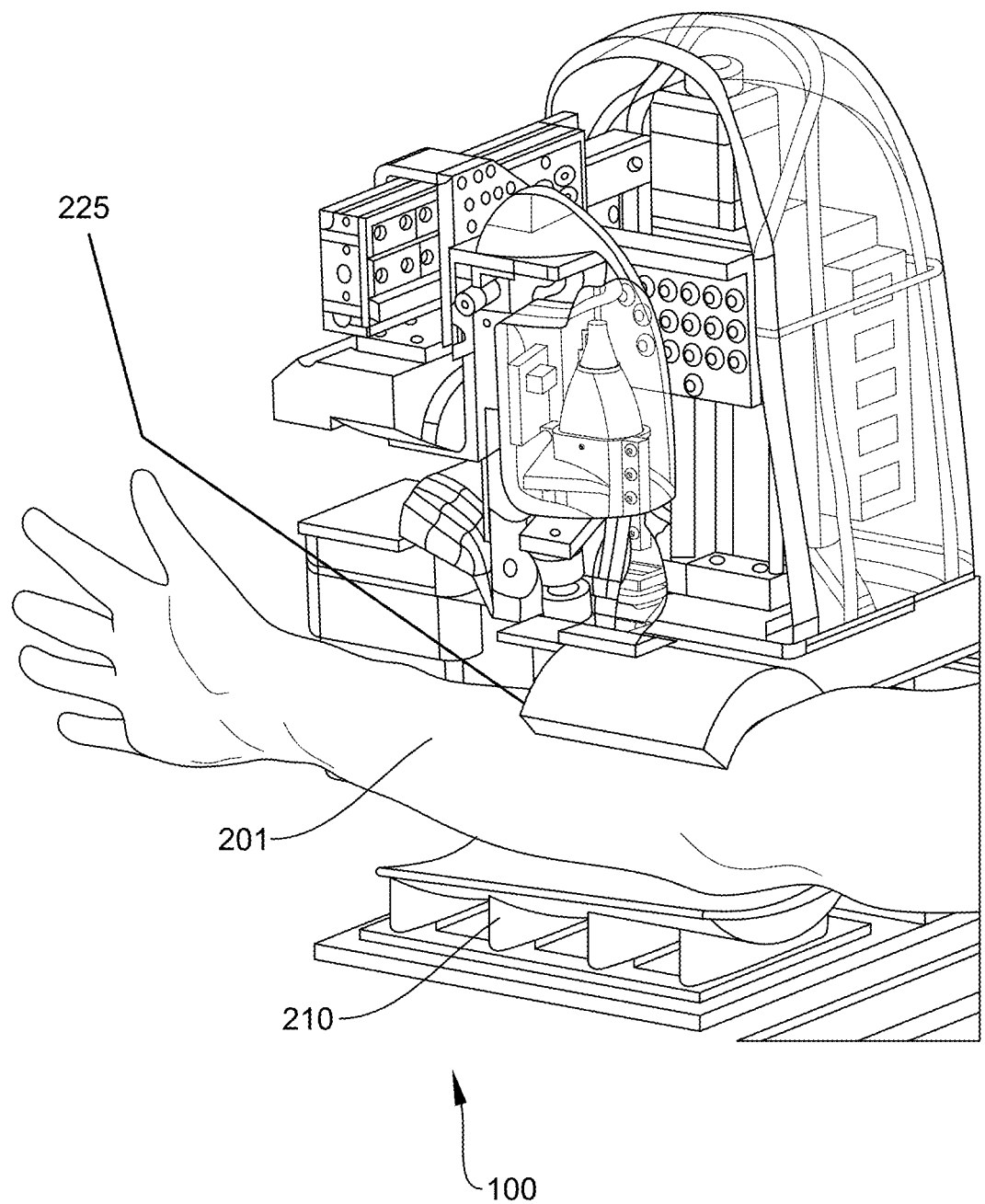
FIG. 2 is another view of the prior art cannulation device in operation.
Figure 3:
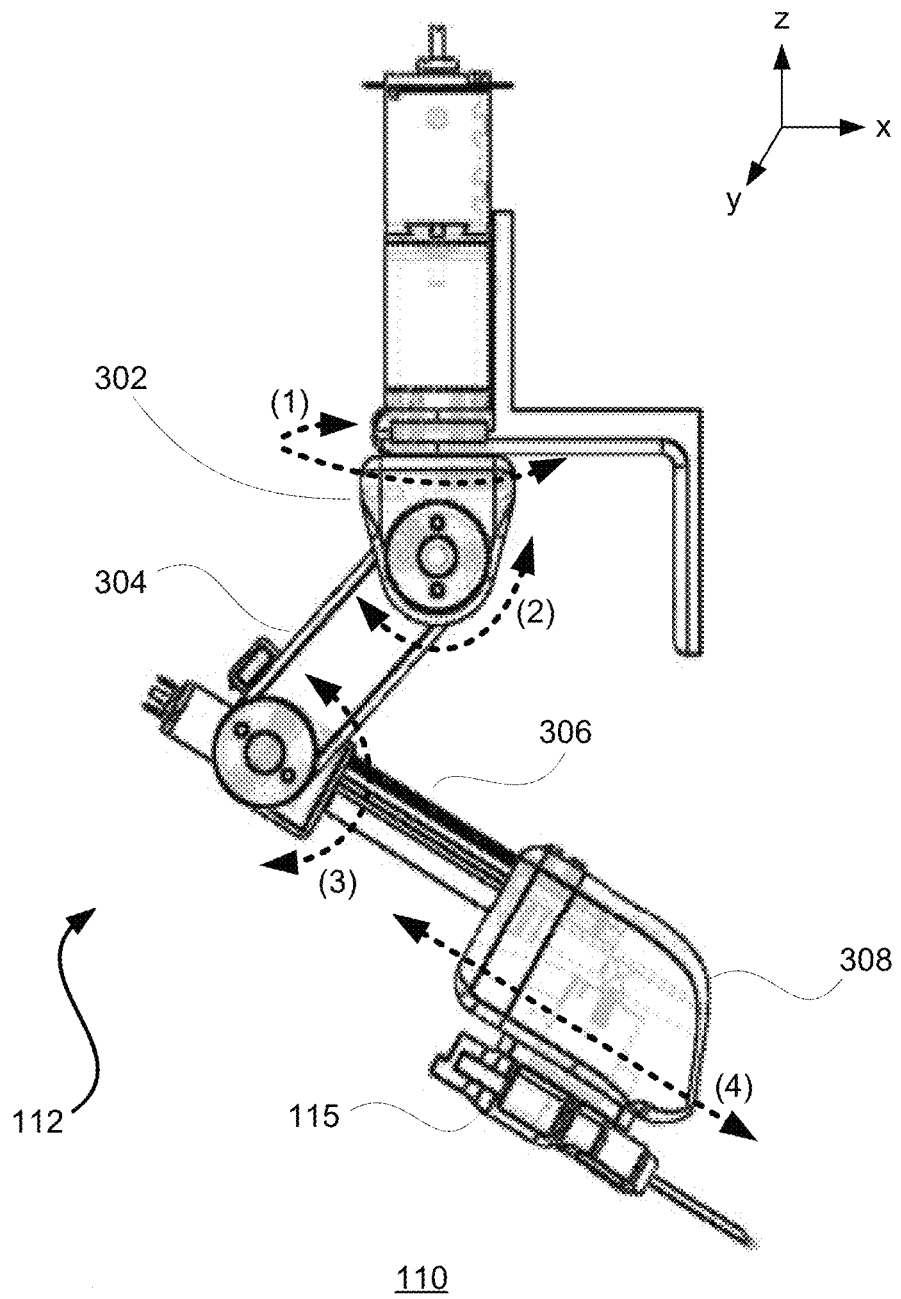
FIG. 3 is an example positioning unit of the prior art cannulation device of FIG. 1.

In some instances, cannulation instrument pose data may be derived from processing data received from an electromagnetic tracker to track movements of the cannulation instrument. Additionally or alternatively, image data (e.g., camera image frames, ultrasound image frames) may be used to the track cannulation instrument pose at it advances towards the target location. In such a case, the images may be processed using a computer vision program. Additionally or alternatively, the cannulation instrument pose data may be derived from the position encoders in each motor. Each joint of the robotic arm's kinematic chain (such as the chain of degrees of freedom shown in FIG. 3) can be defined by a separate pose transformation, starting from the robot origin and ending at the instrument tip.

A pose of the cannulation instrument can be computed from encoder measurements for each degree of freedom or joint and represented by a rotation and a translational offset relative to the previous degree of freedom or joint. The representation can, for example, be in the form of a vector describing the rotation and a translation vector describing the offset. Alternatively, a Euler vector representation may be used to describe the rotation. Otherwise, the rotation and translation representation can be combined into a single homogenous transformation matrix. Whichever the representation, the relative poses of each degree of freedom or joint can be combined in series to obtain a current pose between the origin and the tip of the cannulation instrument.

For example, in the case of a 4 degree of freedom system, a quaternion vector or 4×4 matrix containing position encoder measurements for each degree of freedom can be employed to represent a current cannulation instrument pose. As the motors in the robotic arm manipulate the cannulation instrument, updated encoder information may be provided to one or both of the main processor and the microcontroller, and the transformation chain may be updated based on the updated encoder information.

As explained above, even when the motors cause the cannulation instrument to move, the relative coordinate systems of the imaging unit and the robotic arm remain fixed with one another. In this regard, the order of the transformations T, from the device through a number N of joints in the positioning unit ($joint_1$ through $joint_N$) may be characterized in the following fashion:

$$T_{device\_to\_instrument} = T_{jointN\_to\_instrument} * T_{jointN-1\_to\_jointN} \ldots * T_{joint1\_to\_joint2} * T_{device\_to\_joint1} \quad (1)$$

In this manner, a frame of reference may be defined in terms of the pose and orientation of the device, or particularly a main part of the device. This frame of reference (device) may then be used to relate other parts of the system to one another. For instance, the imaging probe and the cannulation instrument may be related to one another in the following fashion:

$$T_{probe\_to\_instrument} = T_{device\_to\_instrument} * T_{probe\_to\_device} \quad (2)$$

Encoder-based pose measurements may be subject to some residual error. Residual error typically arises due to mechanical imprecision, motor backlash, calibration error, etc. Therefore, in order to reduce the residual error from these measurements, additional sensors may be integrated with the cannulation device. For example, a position sensor (such as that of FIG. 4) can be used to correct for residual error. In one example arrangement, the position sensor may include one or both of a gyroscope affixed to either the robotic arm or the imaging probe to estimate the absolute 3D pose of the cannulation device, and an absolute position/orientation sensor affixed near the distal joint of the cannulation instrument to estimate the absolute 3D pose of the cannulation instrument. Combining the outputs from these two position sensors (e.g., at the main processor) may yield an estimate of relative instrument pose that is not affected by mechanical errors. The transformations used to arrive at the 3D pose of the cannulation instrument relative to the surrounding environment (such as the patient, patient's skin, and the target location, referred to collectively as "world") may be acquired based on the gyroscope measurements, and may be characterized in the following fashion:

$$T_{device\_to\_instrument} = inv(T_{instrument\_to\_world}) * T_{device\_to\_world} \quad (3)$$

Another challenge that arises from the use of the handheld device is the need to characterize the 3D pose of the target vessel relative to the coordinate system of the cannulation device, again as opposed to characterizing the vessel pose based on a fixed coordinate system. That way, if the cannulation device moves, the movement can easily be tracked relative to the target vessel. Additionally, since the cannulation instrument is tracked relative to the cannulation device, manipulation of the cannulation instrument can also easily be tracked relative to the target vessel.

Figure 5:
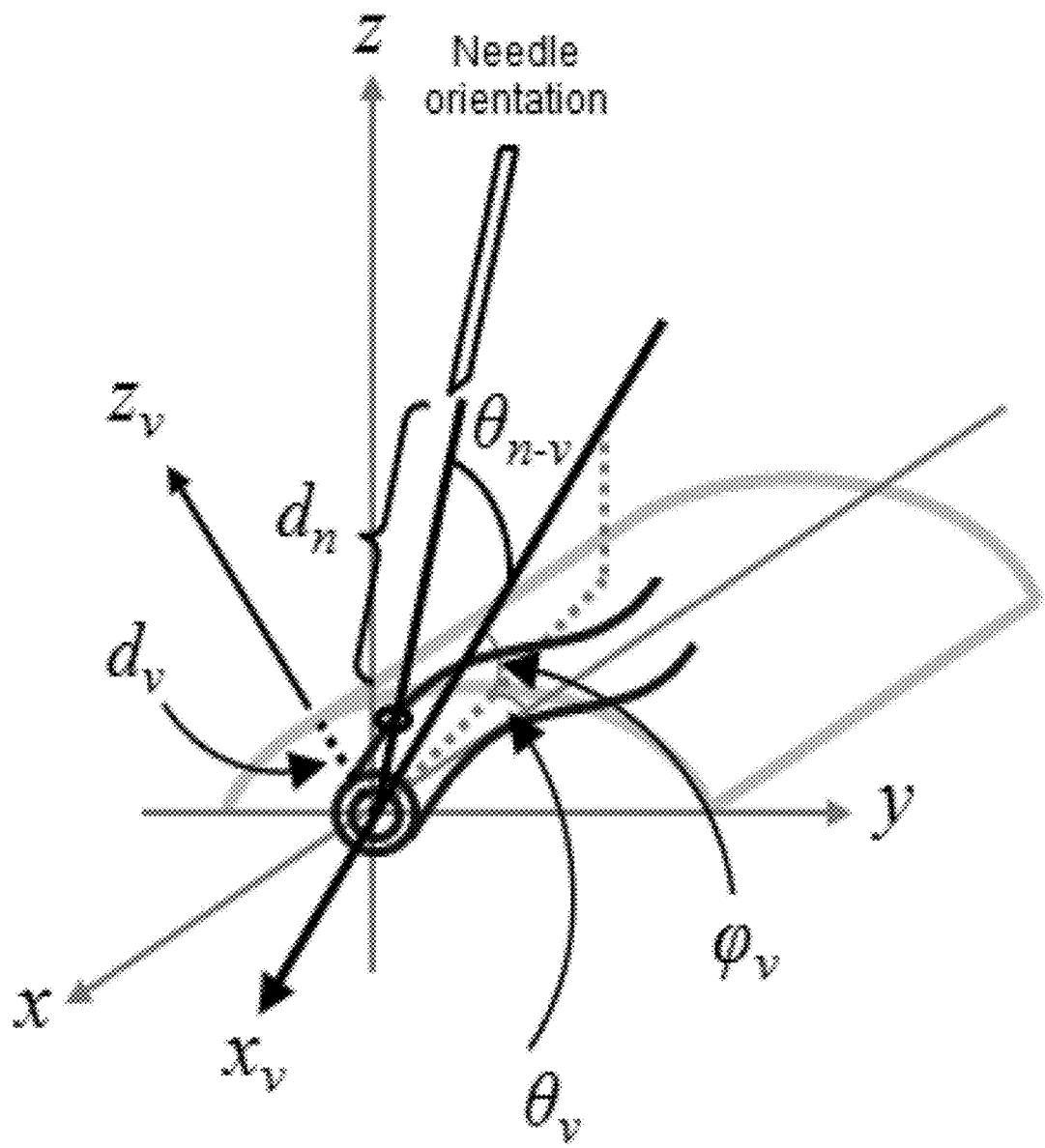
FIG. 5 is an illustration of a vessel and a coordinate reference frame in accordance with an aspect of the present disclosure.

This may be accomplished by relying entirely or primarily on the image data from the imaging probe. There are several ways of performing this characterization, depending on the particular imaging data available. For purposes of clarity, reference is made to FIG. 5, which shows the particular 3D coordinate axes that are useful for characterizing vessel pose.

In a first example, a single two-dimensional (2D) ultrasound image may be obtained in the transverse orientation. From this image, the vessel center can be seen, including its depth from a surface of the patient's skin, through a single cross-sectional plane of the vessel. These correspond to $X_v$ and $Z_v$ in FIG. 5. To confirm that the target location is suitable for puncture, the diameter of the vessel ($d_v$) can be measured from the 2D image. If Color Doppler is used, the blood flow velocity may be quantified. The drawback to the 2D image is that vessel orientation parameters ($\theta_v$ and $\varphi_v$ in FIG. 5) cannot be determined. Therefore, it is assumed that the vessel is horizontal, i.e., parallel with the X axis in FIG. 5. Based on this assumption, a preset insertion angle $\varphi_v$ (e.g., 25 degrees) for the cannulation instrument is provided, and the instrument is inserted along a linear trajectory at the preset angle. If the ultrasound probe is not aligned over the vessel center, or if it becomes misaligned from the vessel center, it can be realigned by translating it along the transverse (Y) direction.

In a second example, a single 2D ultrasound image may be obtained in the longitudinal orientation. In this case, both the depth of the vessel ($Z_v$), as well as the vessel orientation parameter $\varphi_v$, are visible in the ultrasound image. It can also be visualized whether the vessel is straight or curved. A vessel target position $X_v$ may be selected anywhere within the field-of-view of the 2D ultrasound image. The vessel target position may be determined through an automated process, for instance based on a computer analysis of the 2D image. Alternatively, the vessel target position may be selected manually. As with the first example, Color Doppler may be used to confirm the presence of adequate blood flow through the vessel. The drawback in this example is that it cannot be confirmed whether or not the 2D imaging plane cuts exactly through the center of the vessel. In other words, the parameter $Y_v$ in FIG. 5 must be assumed to be at the vessel center, but this cannot be confirmed from the single image slice. The drawback can be overcome by human oversight of the insertion process.

In a third example, multiple 2D images may be obtained in a common orientation, such as the transverse orientation. This may be accomplished via a manual "sweep" of the handheld imaging probe. Vessel orientation in the longitudinal direction may be determined using a "sweep" with the imaging probe along the X axis while keeping the probe in the transverse orientation. The sweep may be relatively short, such as only about 10 mm. Each 2D image acquired during the sweep is then processed and stacked, and a 3D image may be constructed from the 2D slices. Vessel pose parameters, including $\theta_v$ and oy may then be calculated from the constructed 3D image. In this respect, the insertion angle for vessel cannulation may be varied based on the 3D image.

In a fourth example, multiple 2D images may be obtained in the longitudinal orientation. Like in the third example, this may be accomplished using a "sweep" of the probe. The sweep may be relatively short, such as only about 5 mm or less, in order to construct a 3D image from 2D image slices that accurately identifies the center of the target vessel ($Y_v$).

In a fifth example, "bi-plane" ultrasound images may be obtained, as opposed to relying on 2D images. This requires use of a biplane probe, which is capable of acquiring both transverse and longitudinal images at the same time. The simultaneously collected images can then be processed together in order to determine the necessary parameters of the target vessel, including vessel, depth and orientation, as well as identifying the center of the vessel. A trajectory can then be determined for allowing the cannulation instrument tip to be positioned directly above the vessel center and aligned with its axis during insertion and puncture. In this example, a single bi-planar image may be sufficient, although acquiring multiple bi-planar images may improve overall accuracy of the calculations.

In a sixth example, a 3D volumetric ultrasound images may be obtained. In this case, the 3D image provides complete information about the vessel center, orientation, and curvature, from which an optimal trajectory can be determined.

If a 3D volume image is acquired, one or more 2D or bi-planar slices may be extracted from the volume at any arbitrary orientation for display. For example, an oblique slice containing the center of the vessel in the longitudinal orientation may be determined from the 3D volume and displayed as a single 2D image frame. As the probe is moved, the pose of the oblique slice may be updated such that the vessel is always displayed in the resulting 2D image, so long as the vessel is somewhere within the 3D field of view of the imaging probe. Similarly, an oblique slice could be updated to always display the instrument shaft, so long as the shaft is somewhere within the 3D imaging volume. As an extension, multiple slices could be displayed as separate images; for example, an image slice containing the vessel and another slice containing the instrument could be separately displayed.

In addition to the above examples, secondary imaging techniques and equipment may be combined in order to provide any missing information. For instance, camera-based imaging may be used. This can be particularly useful when the ultrasound imaging is unable to provide all of the necessary 3D pose parameters (as is the case for both longitudinal and transverse 2D ultrasound).

For instance, camera-based imaging may be used to determine an orientation of the imaging probe, the cannulation device or both relative to the surface of the patient's skin. One or more cameras may be mounted to the cannulation device, for instance, on a sidewall of the imaging probe, and pointed in the direction of the imaging probe in order to track skin surface features as the device is moved over the patient's skin. With proper camera calibration, the camera images may be used to determine the 3D coordinates of the skin surface relative to the probe. However, it may still be preferable to determine the pose of the target vessel relative to the surface of the patient's skin based on the imaging probe data, since the target vessel is underneath the skin.

Since the camera moves along with the cannulation device, its coordinates must also be transferred in order to properly characterize movement of the patient or the device. The transformation used to arrive at the 3D pose of the patient's skin based on camera image data may be characterized in the following fashion:

$$T_{skin\_to\_device} = T_{camera\_to\_device} * T_{skin\_to\_camera} \quad (4)$$

Camera-based imaging may additionally or alternatively be used to track changes in an orientation of the cannulation instrument, provided that the cannulation instrument is within the field-of-view of the camera. The 3D pose of the cannulation instrument based on camera image data may be characterized in the following fashion.

$$T_{instrument\_to\_device} = T_{camera\_to\_device} * T_{instrument\_to\_camera} \quad (5)$$

Camera-based imaging may additionally or alternatively be used to visualize vessels close to the surface of the patient's skin. Certain wavelengths of light, particularly near-infrared wavelengths (about 700-1000 nm) absorb hemoglobin in blood strongly up to a depth of 4 mm below the skin surface. This results in the acquisition of high-contrast images of the vessels from a top-down view (as seen from the surface of the skin). The 3D pose of the target vessel based on camera image data may be characterized in the following fashion.

$$T_{vessel\_to\_device} = T_{camera\_to\_device} * T_{skin\_to\_camera} * T_{vessel\_to\_skin} \quad (6)$$

Camera-based imaging may also be used to confirm blood flash in the cannula upon puncture: Confirmation of successful puncture has previously been done by visualizing blood flash in the hub of the cannula. However, this is only possible if the cannula hub is visible. Camera imaging, along with display of the camera image on a monitor, provides another way of bringing the cannula hub within view, provided of course that the hub is within the field-of-view of the camera.

The camera-derived parameters can add redundancy to the parameters derived with an imaging probe, such as an ultrasound probe. In some instances, the camera-derived parameters may be used to fill in missing information not obtained from the imaging probe data. However, camera resolution is often an order of magnitude lower than ultrasound resolution; therefore, ultrasound should preferably remain as the primary imaging modality for the technology.

Putting together the imaging data and coordinate transformations described above, the 3D vessel pose relative to the pose of the cannulation instrument may ultimately be characterized in the following fashion:

$$T_{vessel\_to\_instrument} = T_{mainDevice\_to\_instrument} * T_{probe\_to\_mainDevice} * T_{vessel\_to\_probe} \quad (7)$$

This relation between vessel pose and instrument pose is not tied to a particular fixed reference frame, and therefore can easily adapt as the cannulation device is moved about over the target location, or as the target location moves about under the cannulation device.

In some situations, it may be beneficial to first identify a suitable vessel or characterize its 3D pose prior to the start of the cannulation procedure. For example, an initial imaging procedure may be useful to decide whether a cannulation is needed in the first place, to determine a general location for puncture, or to determine the health of a vessel, its readiness to undergo cannulation, or both. In such cases, it may be advantageous to perform imaging scans without having the cannulating instrument fixed to the imaging device, for example to minimize the bulk of the device during the imaging. As such, the imaging unit and instrument positioning unit may include mechanisms to allow for attachment and detachment of the cannulation instrument from the main handheld device. However, when all units are attached to the main device, the coordinate transformations would remain the same as described above.

Yet another challenge that arises from using the handheld device is the need to determine a desired trajectory for the cannulation instrument without relying on a fixed coordinate system. The trajectory determination may begin with a determination of the depth of the vessel underneath the surface of the patient's skin, which is in contact with the imaging probe ($z_v$ in FIG. 5). The orientation of the vessel at the point of cannulation (coordinates $[\theta_v, \varphi_v]$ in FIG. 5) may also be determined. The length of the cannulating instrument may be known, either as a preset value, or as a manually entered value. For some activities, such as blood draw or intravenous cannulation, the cannulation instrument may then be set to a given insertion angle relative to the vessel's longitudinal axis ($\varphi_{n-v}$) based on the determined vessel depth. For example, a vessel that is less than 4 mm deep underneath the skin surface may result in a default insertion angle of about 15 degrees, a vessel between 4 and 8 mm in depth may result in a default insertion angle of about 20 degrees, and a vessel greater than 8 mm in depth may result in a default insertion angle of about 30 degrees. These values are based on recommendations in the clinical practice, but may be further adjusted based on the length of the cannulating instrument.

In some instances, the cannulating instrument may further be aligned rotationally about the vertical axis ($\theta_v$). This may be beneficial if the vessel is not exactly parallel with the longitudinal x-axis. By routing the cannulating instrument, it may be rotated into alignment with the vessel.

In other instances, the main processor may be configured to take additional factors (e.g., patient's age, anatomical location of target vessel) into account in order to determine the trajectory to the target vessel. These factors may be entered manually.

Once the desired trajectory had been established and defined within the cannulation device's coordinate reference frame, the cannula insertion may begin. Throughout the insertion process, the target vessel and its center may be tracked based on continuously acquired image data from the imaging probe, one frame to the next, using image-tracking algorithms. "Continuous" data may refer to data that is received at a frame rate suitable for video capture. Alternatively. "continuous" may refer to the data being acquired at a rate that is faster than the iterative instructions provided to the positioning unit of the cannulation device, as described below. As mentioned above, this "continuous" data capture allows motion—both of the patient and the cannulation instrument—to be detected in real-time, as well as for the cannulation instrument pose to be adjusted accordingly in real-time. Tracking the vessel based on frame-to-frame changes is preferable compared to performing the original determination from scratch for every frame, since it reduces the amount of required computation by the main processor. Other forms of imaging data, such as camera imaging data, may also be used to track motion. Any one or combination of the cannulation instrument, the cannulation device, the patient's skin, and the target vessel may be tracked.

The instrument positioning unit may be iteratively adjusted until the cannulation instrument is properly aligned with the target location. The iterative adjustments may be made to the cannulation instrument by actuators, each actuator controlling a separate degree of freedom (DOF) in the positioning unit. The target location, e.g., the center of the target vessel, may be tracked with each iteration of the image processing routine. When the target location moves, the target location coordinates may be updated according to the coordinate reference frames described above. The trajectory and pose of the cannulating instrument may then be adjusted to account for the updated target location coordinates. This adjustment may also be included with the iteration of the coordinate update. In this way, the instrument positioning unit may operate within a closed loop manner based on continuous image-based feedback to align the instrument with the tissue target.

For example, if the device is being manually moved along a patient's forearm, this movement may result in the depth of the target location changing. This may result in an adjustment to the end-point of the cannulation instrument. Likewise, if the cannulation device is in the middle of the insertion process and it is detected that the target vessel rolls or translates horizontally, the positioning unit may adjust the pose of the cannulation instrument to account for the new coordinates for the target vessel.

There are several ways of adjusting a cannulation instrument trajectory, depending on the DOFs available in the positioning unit and robotic arm. Again, for purposes of clarity, reference is made to FIG. 5, which shows the particular 3D coordinate axes that are useful for defining the changes in the 3D pose of the cannulation instrument.

In a first example, the positioning unit has 1 degree of freedom ($DOF_1$) that controls the insertion distance ($d_n$) (e.g., movement of the cannulation instrument forward and backward). In this configuration, assuming that the trajectory of the cannulating instrument passes through some part of the vessel, iterative adjustments can be made to $DOF_1$ until the instrument punctures the vessel at the point of intersection along the trajectory. If a specific part of the vessel is to be cannulated, the trajectory can be changed by reorienting the positioning unit according to the US image.

In a second example, the positioning unit has 2 degrees of freedom: $DOF_1$ is the same; $DOF_2$ controls the depth of insertion ($Z_n$) (e.g., how deep under the skin the tip of the cannulating instrument will be when it reaches the target location). In this configuration, iterative adjustments can be made to both DOFs. As such, the height of the positioning unit can be adjusted during the insertion process if the trajectory of the cannulation instrument tip becomes misaligned with the target, for example, due to tissue or probe motion.

In a third example, the positioning unit has 3 degrees of freedom: $DOF_1$ and $DOF_2$ are the same; DOF; controls the off-axis position ($Y_n$) of the cannulation instrument (e.g., side to side motion of the cannulation instrument). In this configuration, the positioning device may automatically align the tip of the cannulation instrument with the center of the vessel ($Y_v$, $Z_v$) in the transverse direction. In this regard, the positioning device has the capability to compensate for off-axis (Y, Z) motion, which can arise due to probe movement, tissue motion, or vessel rolling during the puncture. This example configuration could be beneficial when imaging in a transverse probe orientation so that off-axis motions can be automatically detected from the probe image and then iteratively corrected. Thus, these lateral or off-axis adjustments may be useful for correcting lateral movements by either the user or the patient.

In a fourth example, the positioning unit has 4 degrees of freedom: $DOF_1$, $DOF_2$ and $DOF_3$ are the same; $DOF_4$ controls the insertion angle ($\varphi_n$) of the cannulation instrument (e.g., the angle at which the cannulation instrument is tilted downward relative to the surface of the patient's skin). In this configuration, the positioning unit is able to position the cannulation instrument based on a target vessel's depth ($Z_v$), orientation ($\varphi_v$) or both, by independently controlling the angle of insertion. This configuration also enables cannulation to be performed accurately along a nonlinear, curved trajectory. For instance, the device can plot an insertion trajectory that begins the puncture at a relatively steep angle (e.g., 30 degrees) but then gradually decreases the insertion angle to a relatively shallow angle (e.g., 10 degrees) before reaching the target location. The relatively steep insertion angle at the start may be advantageous for reducing the risk of vessel rolling. The relatively shallow insertion angle at the end may be advantageous for reducing the risk of puncturing through the back of the vessel wall of the target vessel. Such adjustments may be particularly important when introducing instruments into pediatric or elderly patients with small and fragile vessels, as well as for high-BMI patients with very deep vessels.

In a fifth example, the positioning unit has 5 degrees of freedom: $DOF_1$, $DOF_2$, $DOF_3$ and $DOF_4$ are the same; DOFs controls the rotational alignment of the cannulation instrument about the vertical axis ($\theta_n$). In this configuration, if the target vessel moves such that the vessel orientation $\theta_v$ is no longer parallel with the longitudinal x-axis, the cannulation instrument may be rotated until its own orientation $\theta_n$ is in parallel with the vessel orientation $\theta_v$. Again, iterative adjustments to $\theta_n$ may be performed in order to compensate for rotational motions, most likely due to probe motion.

In a sixth example, the positioning unit has 6 degrees of freedom: $DOF_1$, $DOF_2$, $DOF_3$, $DOF_4$ and $DOF_5$ are the same; $DOF_6$ controls a longitudinal translation ($X_n$) of the cannulation instrument (e.g., forward and back along an axis orthogonal to the side-to-side motions and the vessel depth axis). In this configuration, the positioning device may be capable of centering the cannulation instrument over any position along the vessel in the longitudinal direction. Once a target position is selected in this direction ($X_v$), the position of the instrument tip ($X_n$) can be set and iteratively moved into alignment with the target position.

The compatibility between each DOF and the corresponding US imaging pose feature is an important aspect in ensuring that the device is usable. For example, it may be advantageous to combine the above-described 3-DOF configuration with a transverse US probe orientation as opposed to a longitudinal orientation. By contrast, if the $Y_n$ DOF is replaced with an $X_n$ DOF, it may be advantageous to use the longitudinal orientation instead of the transverse orientation. Similarly, combining the depth ($Z_n$) and orientation ($\varphi_n$) DOFs enables nonlinear insertion trajectories and may be compatible primarily with the longitudinal probe In some examples, the DOFs of the positioning unit may include one or more remote centers of motion (RCM) positioned about an imaging axis of the imaging unit (e.g., for an ultrasound imaging unit, the imaging axis of the ultrasound transducer). Stated another way, the axis of the RCM may correspond to the axis of the imaging unit, such that any rotational maneuvering of the cannulation instrument about the RCM will be such that the extrapolated cannulation instrument tip position, upon insertion into the target vessel, will be centered below (e.g., within the field of view) of the imaging unit. The RCM may be in addition to the depth of insertion (z axis) DOF, so that various vessels at different depths can be targeted within a single field of view of the imaging unit without requiring movement of the device.

The force sensor (e.g., as described in connection with FIG. 4) may further provide continuous feedback concerning forces exerted on the cannulation instrument. The feedback may be helpful for confirming puncture of the target vessel wall. In an ideal case, the puncture detected by the force sensor should occur at the moment when $T_{vessel\_to\_instrument} \approx 0$, meaning the cannulation instrument tip has just reached the coordinates of the target location.

Feedback from the force sensor may additionally or alternatively be used to control pose of the cannula and the insertion trajectory just prior to vessel puncture. At the time just prior to vessel puncture, the force sensor data may be indicative of vessel motion, such as vessel rolling prompted by pressure applied from the tip of the cannula. Vessel rolling and other forms of vessel motion can cause displacements on the order of less than a millimeter. Nevertheless, these small displacements may be the difference between a successful puncture or a puncture of the vessel sidewall, or even a complete miss of the target vessel altogether.

In order to correct for vessel motion, it is necessary to translate the force sensor feedback into a type of vessel motion. This can be done by providing the force sensor data to either the main processor or microprocessor, and then comparing the force sensor data against pre-stored force data profile information in order to characterize vessel motion.

Figure 6A:
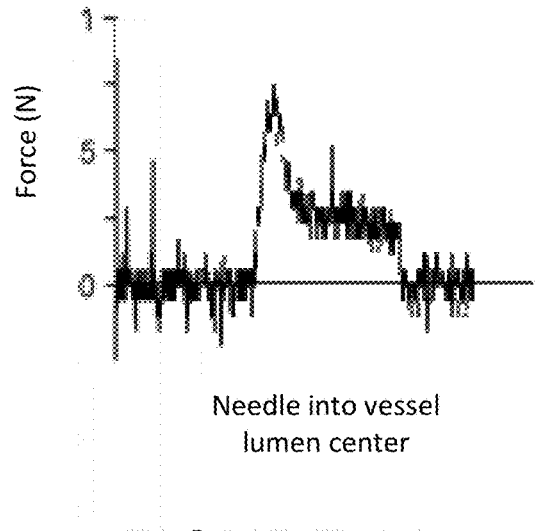
FIGS. 6A-6D are graphical representations of force measurements over time, in accordance with an aspect of the present disclosure.

FIGS. 6A-6D illustrate various force sensor profiles associated with different vessel motions. FIG. 6A shows the profile of a successful puncture. The puncture is characterized by a gradual increase in force on the cannulation instrument over the span of a few seconds, followed by a sharp and sudden increase in force just before puncture, and then followed by a slight decrease in force over the span of several more seconds just after the puncture. Given the profile of a successful puncture, it may be assumed that the vessel did not move during the insertion and puncture process.

Figure 6B:
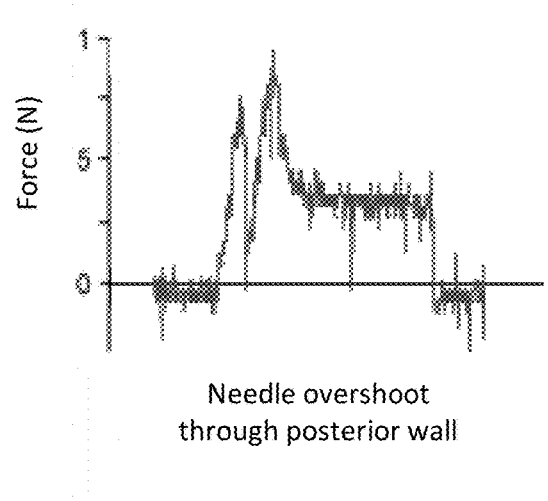

FIG. 6B shows the profile of a cannula overshooting through the posterior wall of the target vessel. The profile is characterized by a sharp and sudden increase in force, followed by a sharp and sudden decrease in force, followed again by another sharp and sudden increase in force, followed by a slower and more gradual decrease in force. Given the profile of an overshoot, it may be determined that one or both of the cannula and vessel has moved out of place. The cannulation instrument may then be repositioned in order to ensure a successful puncture at the center of the vessel.

Figure 6C:
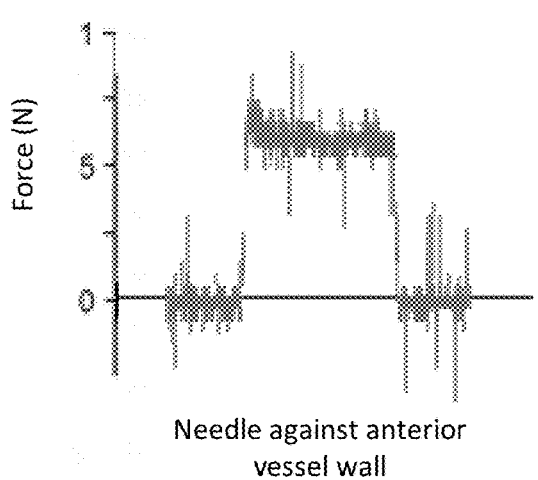

FIG. 6C shows the profile of a cannula resting against the anterior wall of the target vessel. The profile is most notably characterized by a sharp and sudden increase in force, followed by an absence of a decrease in force. Given the profile of an undershoot, the cannulation instrument may be repositioned in order to ensure a successful puncture at the center of the vessel.

Figure 6D:
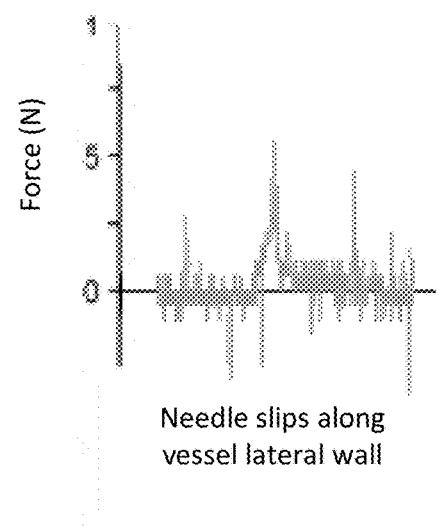

Finally, FIG. 6D shows the profile of a cannula slipping along a lateral wall of the target vessel. A common reason for contact along the vessel lateral wall is vessel rolling caused by the initial contact between the cannula and the vessel. The profile is most notably characterized by a lack of a sharp increase in force, indicating that the vessel wall has moved out of place and not been punctured at all. Given the profile of a missed puncture, the cannulation instrument may be repositioned in order to ensure a successful puncture at the center of the vessel at a further attempt.

In addition to force sensor feedback, other feedback sensor information may be used to characterize a successful puncture. For example, a fluid flash detector may be used to detect an appearance of fluid at a hub of the cannulation instrument (e.g., blood flash for a needle inserted into a vein). A combination of force data may be combined with a detection of fluid flash in order to reach the determination of a successful target puncture. The combination of fluid flash data and force sensor feedback may even be sufficient to guide one operating a handheld venipuncture device to a successful puncture, even for a device having a limited number of degrees of freedom. For instance, for a device having a single degree of freedom, the combination of fluid flash data and force sensor feedback may be sufficient to instruct the device when to stop advancing the cannulation instrument, or when it is necessary to retract or withdraw the instrument due to a failed attempt.

For further example, for a device having no degrees of freedom, the combination of fluid flash data and force sensor feedback may be provided via a display to a clinician in order to improve the clinician's ability to successfully manually advance the instrument towards the target vessel and to not overshoot the vessel. Nonetheless, automating the insertion of the instrument may be beneficial for multiple reasons. First of all, it encourages less movement on the part of the user as the instrument is being inserted. Furthermore, it allows greater control over the speed at which the instrument is inserted. Differences in insertion speed may influence puncture forces exerted on the instrument, whereby greater speeds may reduce the forces exerted and slower speeds may result in increased forces. Having control over the speed of insertion, such as to ensure a sufficiently slow insertion, may allow for more accurate force measurements to be collected.

Figure 7:
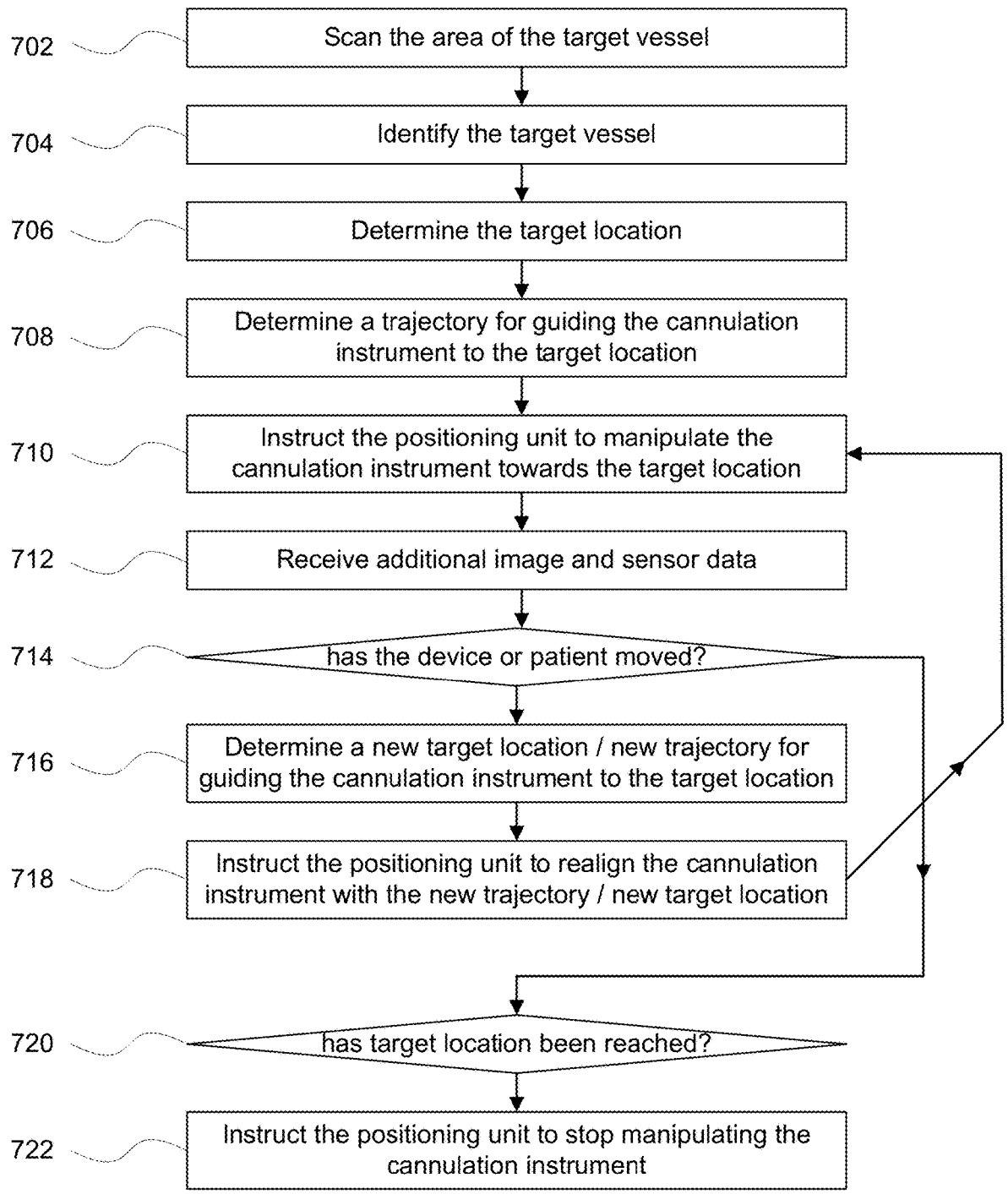
FIG. 7 is a flow diagram of a protocol according to an aspect of the present disclosure.

FIG. 7 is a flow diagram of an example protocol 700 for executing an automated method of aligning the trajectory of a cannulation device with a target location.

At block 702, the imaging probe is used to scan an area around the target vessel. As explained above, scanning may involve collection of a single 2D image in one plane, multiple stacks of 2D images in one plane, single 2D images in multiple planes, or other combinations of 2D images. Additionally, in some instances, because the imaging probe is mounted to a handheld cannulation device, the probe may be swept over the area around the target location, the imaging data may then be stitched together to yield a 3D image of the target.

At block 704, a target vessel in the scanned area is identified. The target vessel may be identified manually, or with the aid of an imaging device, such as an ultrasound imager or camera.

At block 706, a processor of the cannulation device determines a final position of a tip of the cannulation instrument. The final position is generally a center point in the target vessel. The final position may be defined in terms of the vessel geometry, including spatial [x,y,z] coordinates of the vessel, and further including polar [θ,φ] coordinates of the vessel's rotation.

At block 708, the processor determines a trajectory for guiding the cannulation instrument to the final position. The trajectory is based on a current pose and location of the cannulation instrument, as indicated by position encoders associated with the motors of the positing unit for manipulating the cannulation instrument. Additionally, various aspects of the trajectory may be controlled by separate motors, each motor itself associated with a different degree of freedom (DOFs) for manipulating cannulation instrument. Various DOF axes, and the impact of manipulating the cannulation instrument along such axes, have been described above.

At block 710, the processor may provide instructions to the positioning unit to manipulate the cannulation instrument towards the final position. This may involve positioning the cannulation instrument in alignment with the target location, manipulating the cannulation instrument along a trajectory towards the target location, or both.

In some examples, the instructions at block 710 may be provided iteratively, meaning that the positioning unit is instructed to move the cannulation instrument an incremental step towards the target location, but not necessarily all the way to the target location. Iterative positioning allows for the processor to receive more imaging data, process the newly received imaging data, and make corrections to the target location, trajectory or both before the positioning unit continues manipulating the cannulation instrument. In this regard, operations may continue at block 712 with the processor receiving additional image or other sensor data, such as feedback data from a force sensor or position sensor. Then, at block 714, the processor determines whether either or both of the cannulation device (e.g., the cannulation instrument, the imaging probe) or the patient (e.g., the skin of the patient, the target vessel of the patient) have moved in a manner not consistent with the instructions provided to the positioning unit. If no movement is detected, operations may continue at block 710 with the next iteration of instructions to the positioning unit, or at block 720 described below.

Otherwise, if movement is detected, then at block 716, a new target location, new trajectory or both may be determined. In order not to make the determinations from scratch, the detected movement may be characterized in terms of the previously collected data, and particularly in terms of the coordinates by which the previously collected data was defined. Then, at block 718, the processor may instruct the positioning unit to realign the cannulation instrument with the new target location, manipulate the cannulation instrument along the new trajectory, or both. In some instances, the processor may be configured to determine one or more axes over which the movement occurred, and then provide instructions to the particular motors of the positioning unit that control motion along the determined axes. As with block 710, the instruments may be provided iteratively. Operations may then continue at block 712.

At block 720, the processor may determine whether the tip of the cannula in the cannulation instrument has reached the target location. If the target location has not been reached, operations may continue at block 710 with further iterative movement towards the target location. If, however, the target location has been reached, operations may optionally continue at block 722 with the processor instructing the positioning unit to stop, such that the cannulation instrument stops moving. The processor may determine when the target has been reached by tracking the pose of the target and instrument, and further by analyzing the force sensor information. By iteratively tracking a position, orientation or both, of both the instrument tip and target center, the processor can ensure that the instrument has reached the target when the two tracked values converge. Furthermore, the force sensor may provide an instantaneous, binary confirmation of a target puncture.

In some examples, the determination of a successful or failed target puncture may be binary, whereby the cannulation instrument stops moving upon success, and a trajectory may be adjusted upon failure in order to retry the cannulation attempt. Alternatively, a likelihood of success or failure may be determined, and the trajectory may be adjusted in a manner that increases the likelihood of success and/or reduces the likelihood of failure. In this manner, adjustments may be made to the cannulation instrument trajectory even in the middle of an insertion attempt, and before insertion is determined to succeed or fail.

The mid-insertion determination may be made using a machine learning algorithm that is programmed to predict whether the target puncture will or will not be successful. The algorithm may be trained on logged data recorded from previous puncture attempts from the same device or similar devices. The logged data may include an indication of whether the attempt was successful or unsuccessful, as well as other collected data including, but are not limited to, image data (e.g., ultrasound information to track vessel movement), force sensor feedback, cannula pose data, device pose data, etc. Then, during the current session, the same or similar data may be collected from the device sensors and probes, and used to predict a likelihood of success or failure. The program may further be configured to analyze how the likelihood of success or failure by manipulating the cannulation instrument (e.g., advancing a depth of the cannulation instrument, moving the instrument to the left or right, changing a pitch of the instrument, etc.). The program may further determine whether any of the analyzed adjustments most favorably improves the likelihood of success (or minimizes the likelihood of failure), whereby the processor may control manipulation of the cannulation instrument accordingly.

In some cases, the machine learning algorithm use a multivariate learning process, such as classification, regression, clustering, to categorize the training data, and then determine which class the current data falls within, as well as a likelihood of the classification being correct. In other cases, the machine learning algorithm may use a neural network to process the many raw inputs into a single probability output of success/failure.

To illustrate the machine learning-based routine, the following example application is provided. If during the insertion but before the moment of vessel puncture, the vessel may begin to roll out of position of the insertion path. The vessel roll may be detected using one or more sensors, including the ultrasound imaging, and the force sensor. However, it may be difficult to characterize the vessel rolling with perfect certainty until after the fact. Thus, instead of recognizing vessel roll after the fact, the machine learning algorithm can predict in advance that the vessel is likely to roll out of the trajectory, and may immediately adjust the trajectory of the cannulation instrument with the target vessel in order to minimize the likelihood of the vessel roll actually occurring.

Figure 8:
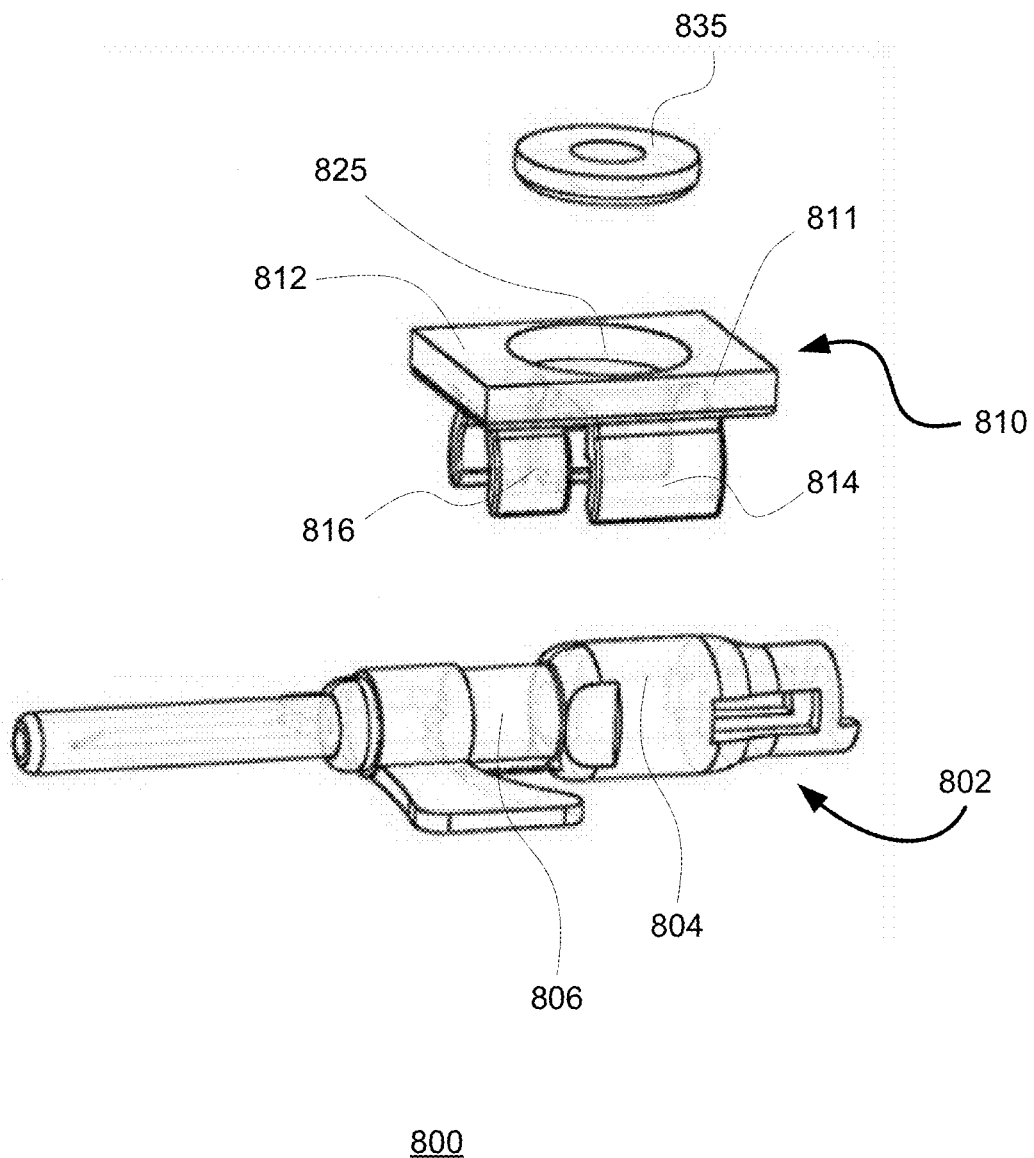
FIG. 8 is an exploded perspective-view diagram of an electromagnetic attachment mechanism in accordance with an aspect of the disclosure.

The above examples generally describe attachment of a cannulation instrument. The instrument may be, for example, a needle or catheter, depending on the particular application at a given time. Additionally, the cannulation device may be designed to receive several different types of cannulating instruments. For instance, a robotic arm of the device may be designed to receive either one of a needle or a catheter. The manipulators for each of the needle and catheter may further be designed such that each is compatible with the same robotic arm, such that one instrument may be easily detached from the instrument, and the other attached. The instruments may be attached and detached using an electromagnet-based attachment component. An example electromagnet-based attachment component is shown in the exploded view of FIG. 8, using attachment of a blood collection needle 802 for the sake of example. The blood collection needle 802 has a substantially cylindrical shape, having a first segment 804 with a relatively wider diameter that tapers to a second segment 806 with a relatively narrower diameter. An adapter 810 is configured to clip onto the needle 802 at each of the first segment 804 and the second segment 806. Specifically, the adapter 810 includes an upper member 811 having a flat top surface 812 and two clips 814 and 816 attached to a bottom surface. Each of the clips 814 and 816 is adapted to engage with a respective segment 804 and 806 of the needle 802. A middle portion 825 of the upper member is hollowed out, and a steel plate 835 is inserted into the middle portion 825. The steel plate is configured to engage an electromagnet included in the robotic arm (not shown). This design may be utilized to enable quick removable attachment of various cannulation instruments, so that the use of a single cannulation device may easily be switched from, for instance, catheterization to insertion of a needle.

The attachment component may allow for the handheld device to be easily compatible with conventional needles and/or catheter insertion devices. For instance, angle adjustments between 0 to 70 degrees, injection forces of 0-15 N, and insertion depths of 0-100 mm, may all still be possible, depending on the type of vascular access that is being performed.

In the above examples where an ultrasound transducer is used, a gel attachment component may be used that attaches to the head of the transducer, providing a source of acoustic coupling when the transducer is in contact with the skin. The gel attachment component may consist of a clip that holds acoustic coupling gel. Additionally, the acoustic coupling gel may be formulated to contain an anesthetic drug that is designed to release via ultrasonic energy, thereby numbing the insertion site before the puncture. The gel attachment component may also be used to stabilize the vessel or other tissue target. Furthermore, the gel attachment component may flex and conform to patient arm geometry. Finally, the ultrasound gel attachment component and instrument attachment component of FIG. 8 may be incorporated within a single disposable housing unit. In this fashion, the ultrasound and instrument attachment components may be attached to the handheld device in a single motion. For example, the two components may be fixed at a preset geometry within the disposables housing unit, such that when the device is positioned and lowered over the disposables housing unit, the instrument attachment component engages with positioning unit, and the ultrasound gel attachment component engages with the ultrasound imaging unit.

Figure 9A:
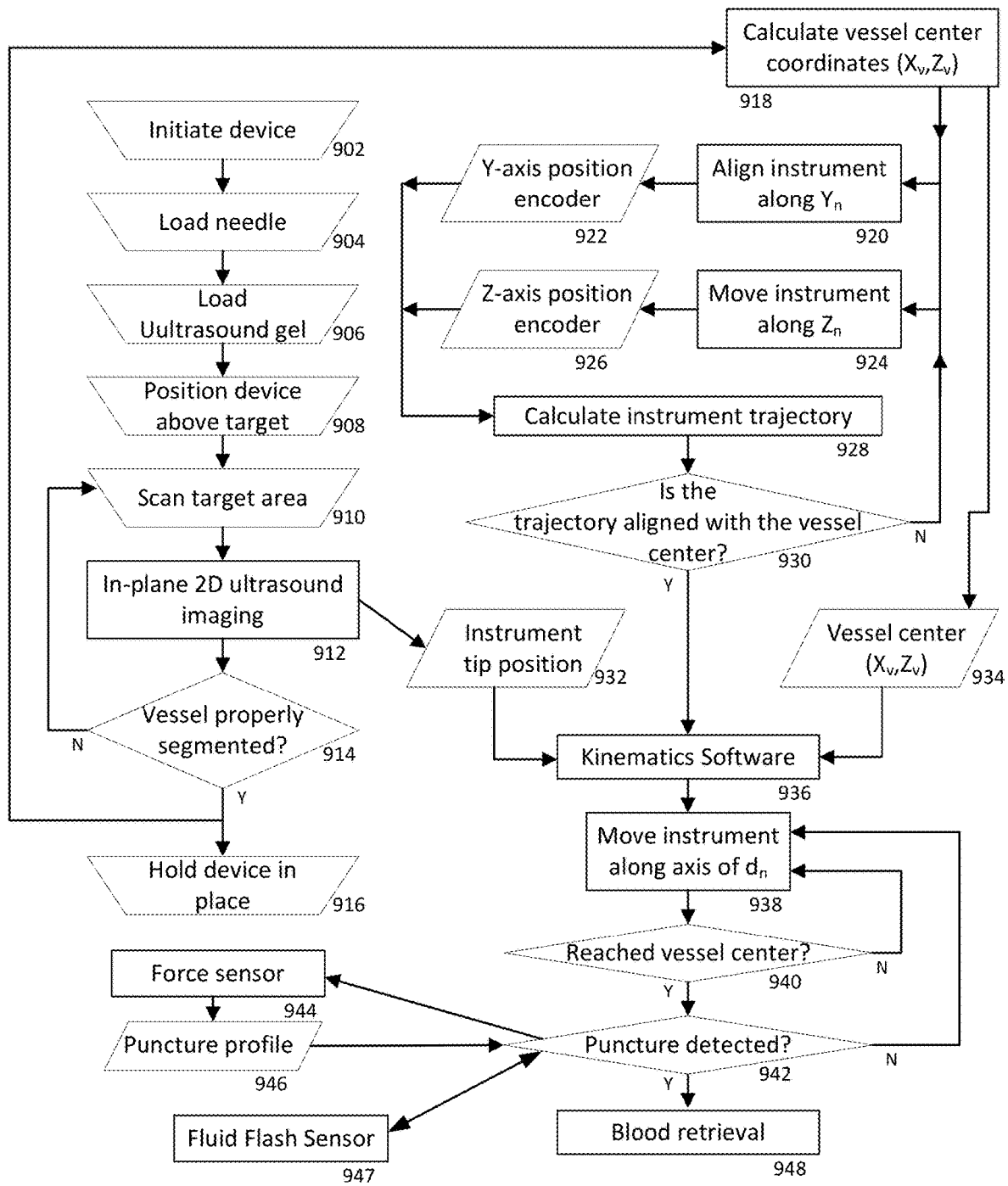
FIGS. 9A-9C are flow diagrams of additional protocols in accordance with aspects of the present disclosure.
Figure 9B:
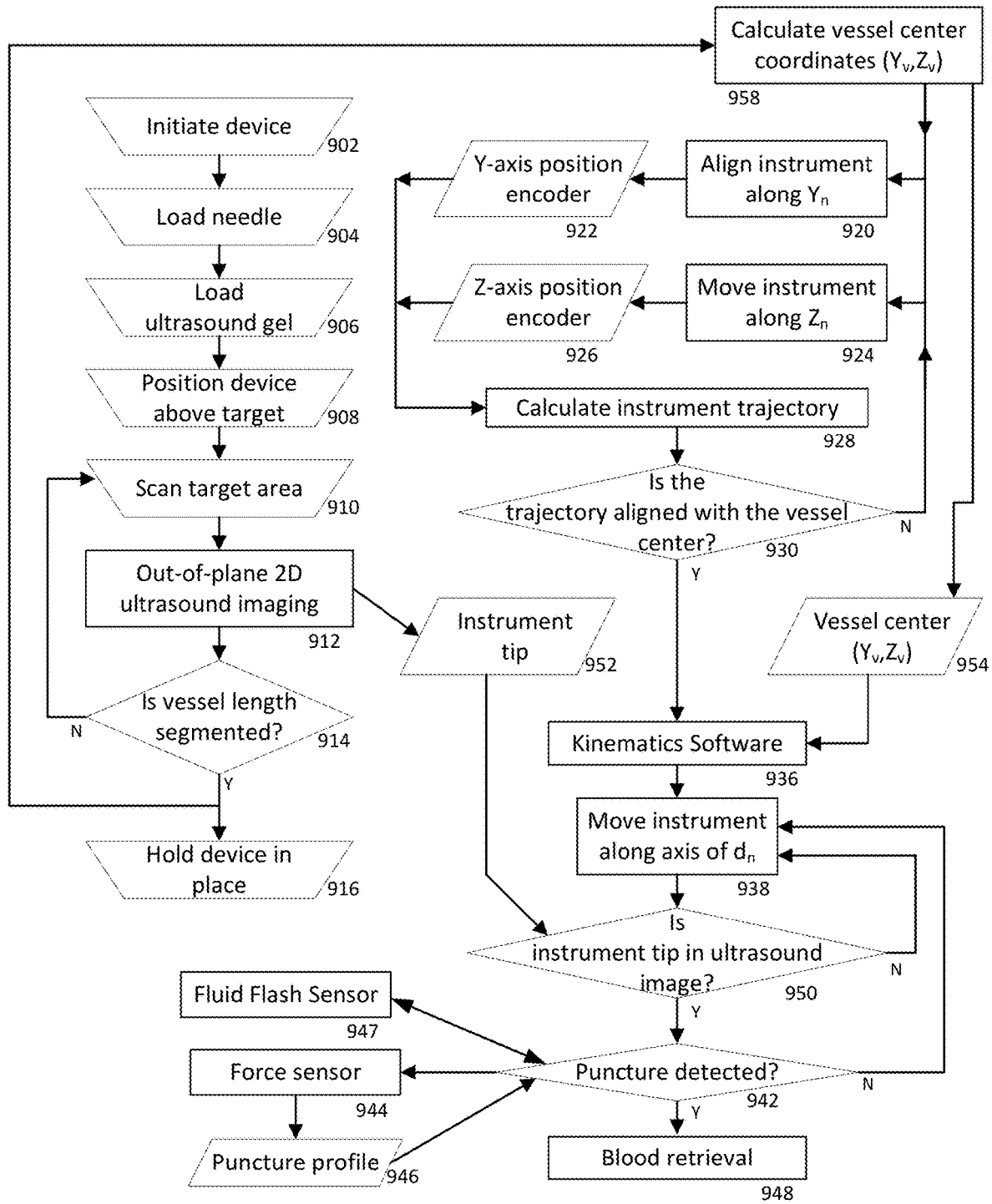
Figure 9C:
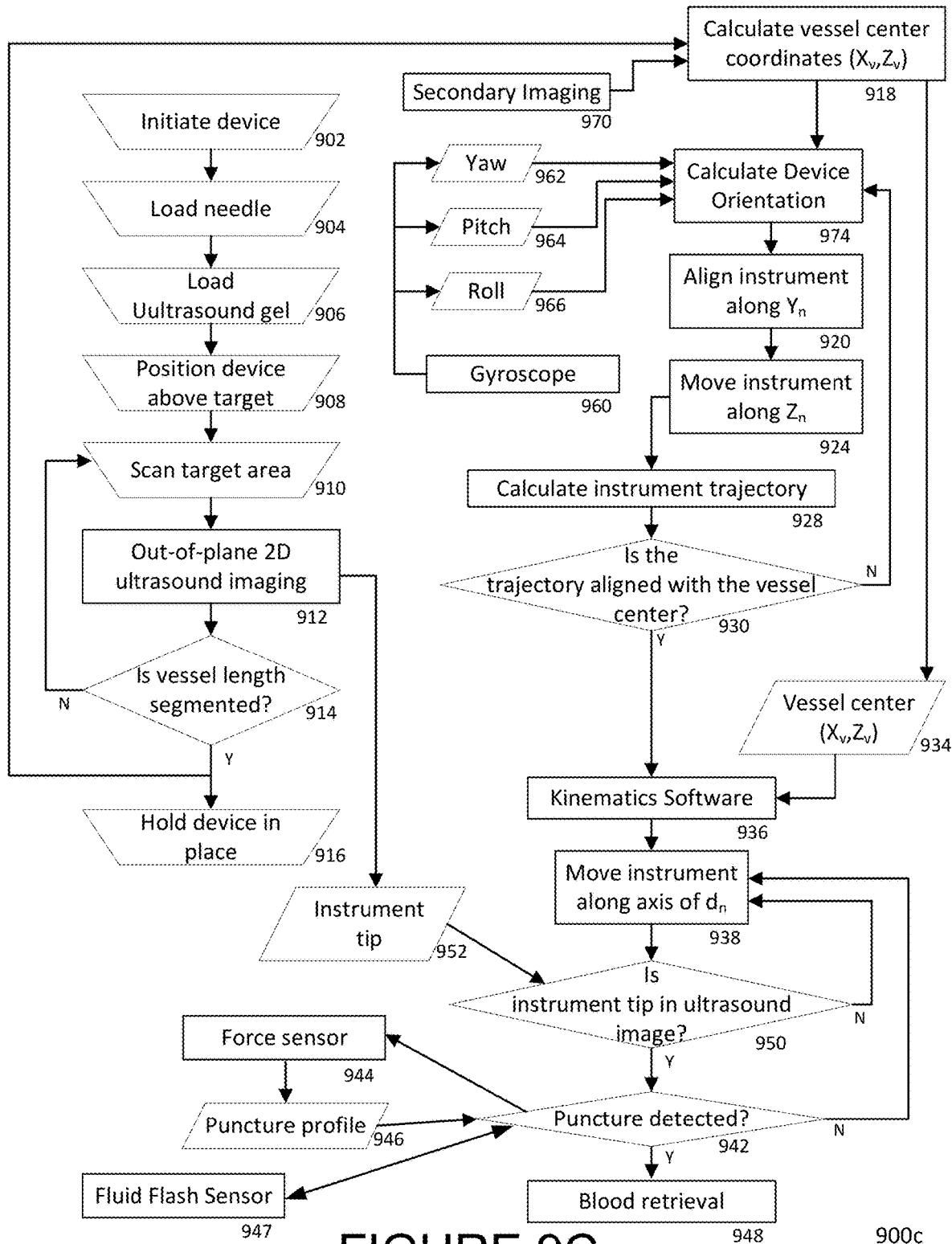

The above examples generally describe protocols for a device using an out-of-plane imaging approach for tracking insertion of a cannulation instrument. However, similar methods and protocols may be applied for in-plane imaging techniques, in which the cannulation instrument is present in the image even before reaching the target location. FIG. 9A-9C are flow diagrams of three example protocols 900a, 900b and 900c for executing various automated methods of aligning the trajectory of a cannulation device with a target location depending on whether the imaging approach is in-plane or out-of-plane, and further depending on the particular inputs that are available for tracking the alignment. Each of the examples relies on two dimensional ultrasound imaging as a primary source of image data, but the two dimensional imaging in the example protocol 900a of FIG. 9A is in-plane, whereas the two dimensional imaging in the example protocols 900b and 900c of FIGS. 9B and 9C, respectively, is out-of-plane. Additionally, protocol 900c relies on data received from a gyroscope and from a secondary imaging source (e.g., camera), whereas protocol 900b does not.

With attention to FIG. 9A, protocol 900a begins with several manual preparation steps, including initiating the device (902), clipping the desired cannulation instrument to the device (904), loading a gel attachment to the device (906), and placing the device in position to image a target area (e.g., above the target area) (908). In some instances, the target area can be manually scanned for a suitable insertion site (910). During the aforementioned imaging process, two-dimensional ultrasound images may be captured by the device (912). As described above, these images may be continuously captured, such as in real time, to provide feedback about movement of the target or the device in the imaged target area.

A vessel (e.g., vein) in the ultrasound image may be segmented in order to ensure tracking of the vessel in subsequent images. The device may check whether the vessel in the captured image is properly segmented (914), and if not wait for additional scans of the target area to be obtained and processed (910, 912). If the vessel is properly segmented, then a user of the device may attempt to hold the device in place (916) instead of scanning for a new target location, and operations may continue with calculation of the center coordinates of the segmented vessel (918). Data of the coordinates (934) may be stored for later use.

Using the vessel coordinates, the motors for positioning the instrument may be controlled to bring a trajectory of the instrument into proper alignment with the target location, e.g., a vessel center. This may involve either or both of operating a motor for controlling the Y-axis alignment of the instrument (e.g., along axis $Y_n$, described above as $DOF_3$) (920) and operating a motor for controlling the Z-axis or depth-of-insertion positioning of the instrument (e.g., along axis $Z_n$, described above as $DOF_2$) (924). The motor operations (920, 924) may be tracked by respective position encoders (922, 926).

A trajectory for moving the instrument to the vessel center may be calculated (928), and further it may be checked whether the calculated trajectory is in alignment with the vessel center (930). If the alignment is not correct, then operations may revert to controlling the motors (920, 924) in order to bring the instrument back into alignment and recalculating a trajectory for moving the instrument to the target location (928). As explained above, this tracking may be continuously performed, in case either the target vessel or the device unexpectedly moves. However, for purposes of clarity, the trajectory alignment tracking is shown only once in the protocol.

Provided the trajectory is properly aligned, then the kinematics software (936) included in the processor may begin to move the instrument along its axis of insertion (938) based on the vessel center coordinates (934) and further based on image data collected from the ultrasound images indicating a location of the instrument's tip (932). The instrument may be moved iteratively, regularly checking whether the tip has reached the vessel center, e.g., based on the ultrasound imaging (940). If the instrument tip has not yet reached the vessel center, the instrument may be moved further forward along its axis of insertion (938). Otherwise, if it is determined that the instrument has reached the vessel center, or more generally the target location, then operations may continue with the designated function of the cannulation instrument (e.g., blood retrieval) (948).

Optionally, the determination of whether to commence the designated operation of the cannulation instrument may be further based on force data from a force sensor (944). For instance, the processor may determine whether the cannulation instrument has properly punctured the vessel (942) based on force sensor data (944). For instance, the force sensor data can be classified based on several profiles (946), and if the profile of the force data matches a profile indicating a proper puncture, then operations may continue with the designated function of the cannulation instrument (e.g., blood retrieval) (948). Additionally or alternatively, the processor may determine whether the cannulation instrument has properly punctured the vessel (942) based on fluid flash data (944), such as feedback from a blood flash sensor in the case of blood vessel cannulation. For instance, if the fluid flash data indicates a presence of fluid flash in the cannulation instrument, it may be a sign of a successful cannulation, and then operations may continue with the designated function of the cannulation instrument (e.g., blood retrieval) (948). Otherwise, if the force sensor data is classified as a different type of profile, such as vessel rolling or overshooting a vessel wall, or if no fluid flash is detected, or any combination of feedback data, then operations may continue with the instrument being moved back along its axis of insertion (938). In other cases, success of the cannulation may be further based on cannula pose information, which may be image data (such as from the ultrasound imager) or motor feedback data With attention to FIG. 9B, protocol 900b is similar to protocol 900a except that the ultrasound imaging (912) is performed out-of-plane instead of in-plane. As a result, the image of the target location does not feature the cannulation instrument until later in the insertion process. When the instrument tip is eventually located in the image (952), its location is detected (950), and may be used as an indication of whether the instrument has arrived at the target location so that the cannulation operation (e.g., blood retrieval) may begin (948).

Additionally, in protocol 900b, the vessel center coordinates are defined in terms of the Y and Z axes of the vessel (958), as opposed to the X and Z axes as described in protocol 900a. The Y and Z axis coordinates are then stored (954) as inputs for the kinematics software (936) used to drive the cannulation instrument towards the target location (938)

With attention to FIG. 9C, protocol 900c is similar to protocol 900a in that vessel center coordinates are defined in terms of the X and Z axes of the vessel (918), and similar to protocol 900b in that the ultrasound imaging is performed using an out-of-plane approach. Protocol 900c differs in that each of a gyroscope 960 and secondary imaging device (e.g., camera) (970) are provided to enhance the tracking of the device's orientation and calculation of the vessel coordinates, respectively. The gyroscope collects data, such as an absolute orientation of the device, which in turn may be indicative of the yaw (962), pitch (954) and roll (966) of the device. The secondary imaging device (970) may image the target location, including the target vessel, in order to improve tracking of the vessel and provide more accurate information, or a second set of information to check against the data from the primary imaging source, regarding the whereabouts of the target vessel. In the case of the gyroscope data, the collected data is provided as inputs to calculate and monitor the device orientation (974), which can then be used to align the cannulation instrument with the target location (920, 924) and further to calculate and track the trajectory of the cannulation instrument towards the target location (928, 930).

In other example protocols, the tracking of device orientation using a gyroscope and secondary imaging device may be performed in connection with in-plane imaging techniques, tracking of Y and Z axes of the vessel coordinates, or both.

The above examples demonstrate control algorithms and designs for automating venipuncture and other cannulation methods using a handheld device. However, it should also be appreciated by those skilled in the art that the handheld device can also be used manually, if so preferred. Furthermore, a combination of manual inputs and automated control may be preferable. For instance, a clinician may be tasked with selecting a preferred vein of the patient, while the automated process is used to determine the precise target location within the selected vein. For further instance, if a patient moves during the process, a clinician may choose to terminate the cannulation process without having to wait for the device to detect the patient's movement. The clinician may further observe image data over the device's display in order to ensure that the automated process is being carried out correctly.

The device may also include a combination of manual inputs and automated control. Specific form factors of the device may be chosen to permit freehand use, in which all degrees of freedom are manually controlled. Other form factors may be chosen for imaging only, in which the cannulation unit is removed; or for imaging to be used to guide the needle insertion; or for attachment to a passive support arm, which provides a fixture to the device; or for automatically orienting the device so that the needle aligns with the vessel, followed by manual insertion; or for manual orientation of the needle to align with the vessel, followed by automated insertion; or for automatically orienting the needle while at the same time permitting for manual adjustments, followed by either automated or manual insertion.

Figure 10A:
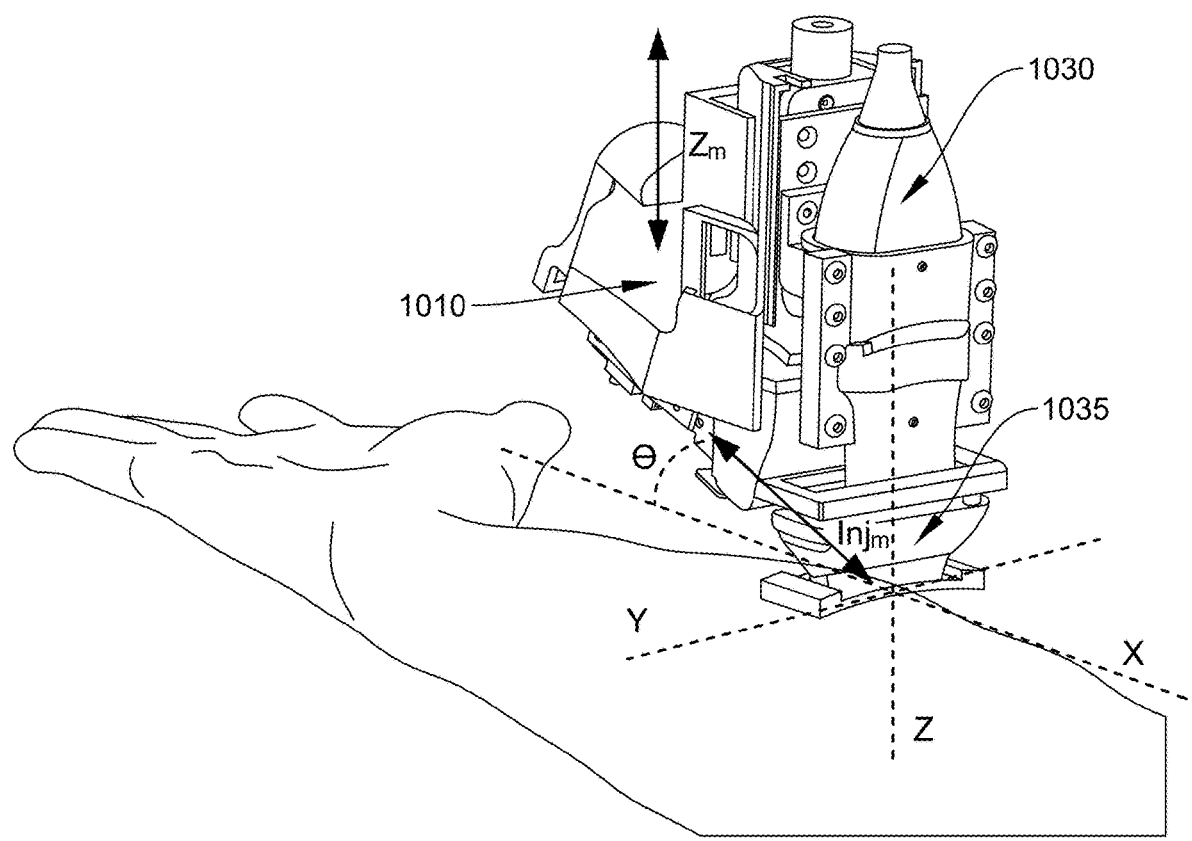
FIG. 10A is a perspective view of a cannulation device in accordance with an aspect of the present disclosure.

FIGS. 10A-10I show an example of a device having two degrees of freedom: height ($z_m$) and depth of insertion ($Inj_m$). In the example of FIG. 10A, the height may be controlled by a motor capable of translating the needle 1080 along a direction of the Z-axis. The depth of insertion may be controlled by a motor capable of translating the needle in a lengthwise direction of the needle within the X-Z plane. In some examples, a pitch $\theta$ of the needle within the X-Z plane may be adjusted or may be fixed.

The device 1000 includes on one side a manipulator 1010 and on another side a probe 1030, such as an ultrasound probe. The probe 1030 may be mounted to the manipulator 1010, such as by a mounting frame 1025 (see FIG. 10B). In the case of an ultrasound probe, a clip 1035, such as for holding gel, may be mounted to a bottom portion of the probe 1030.

Figure 10B:
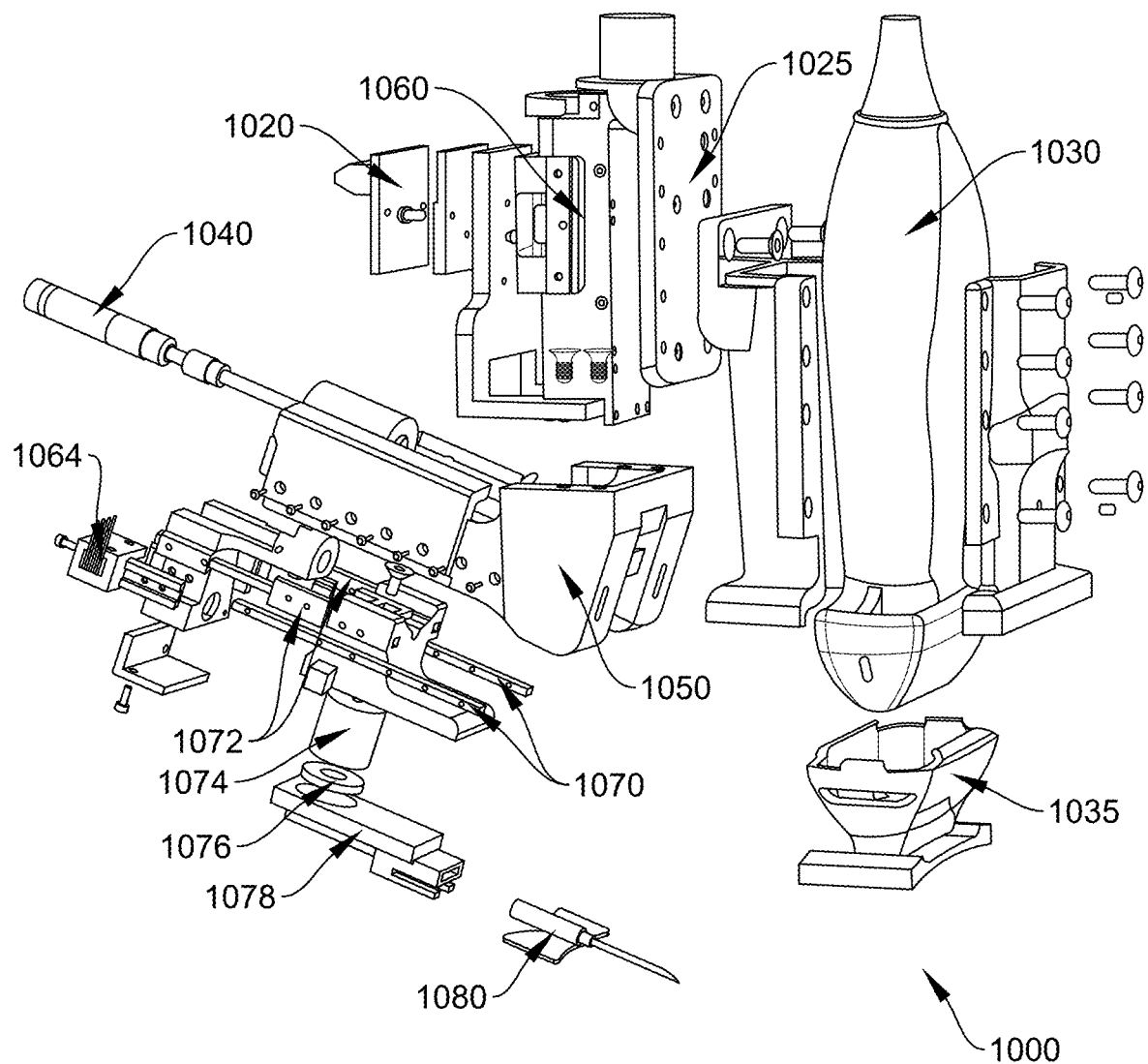
FIG. 10B is an exploded diagram of the cannulation device of FIG. 10A.

As shown in FIG. 10B, which is an exploded diagram of the device 100 of FIG. 10A, the manipulator 1010 may include a housing that contains therein a first motor 1060, such as a linear stage DC motor, for controlling a position of the device in the height direction. The height of the device may be considered as a height of the manipulator 1010 in relation to the probe 1030, since the bottom of the probe 1030 (e.g., the bottom surface of clip 1035) may rest on or close to the patent in order to provide proper imaging of the target location. The housing of the manipulator 1010 may also contain one or more processors 1020, such as a microcontroller, for controlling operation of the manipulator. The needle 1080 may be housed in a needle insertion housing 1050 that is positioned under the manipulator 1010 housing. Also contained within the needle insertion housing 1050 may be a second motor 1040, such as a spindle drive motor, for controlling a depth of insertion of the needle.

As can be seen from FIG. 10B, the needle insertion housing 1050 may also contain therein guide rails 1070 for guiding the insertion motion of the needle 1080 as the second motor 1040 drives the needle. A pair of ball bearing carriages 1072 may be coupled to the guide rails 1070 to allow the needle 1080 to be slidably mounted to the guide rails 1070, under the control of the second motor 1040.

Additionally, one or more sensors may be provided in order to provide feedback regarding the position of the device, the needle 1080, or both, as well as progress of the cannulation. For example, a force sensor 1064 may be provided to detect an amount of force exerted on the needle during insertion. Additionally, a gyroscope and accelerometer may be included in the microcontroller 1020 in order to track pose and orientation of the device.

The needle may be removably attached to a clip 1078, which in turn may be affixed to an electromagnet 1074 by a washer 1076. The electromagnet may enable easy insertion and removal of the needle clip from the needle insertion housing 1050.

Figure 10C:
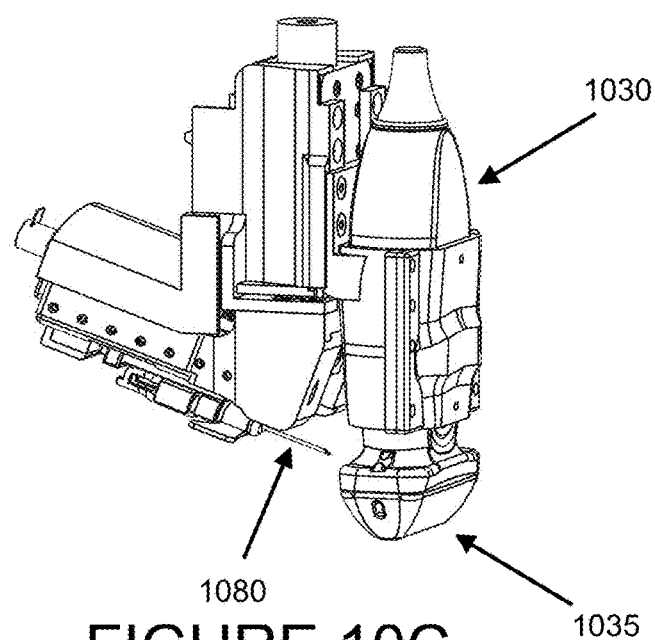
Figure 10D:
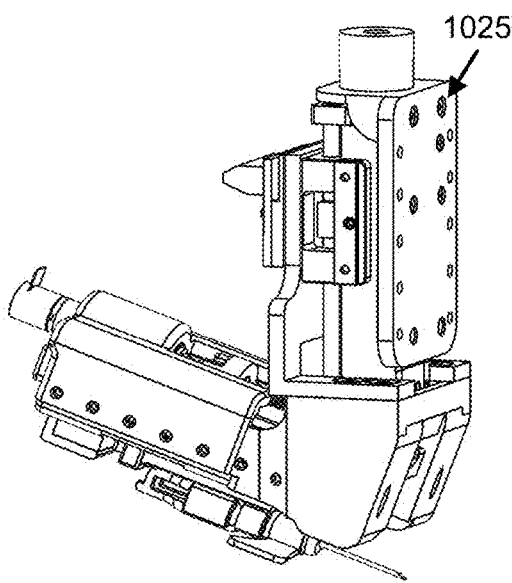
Figure 10E:
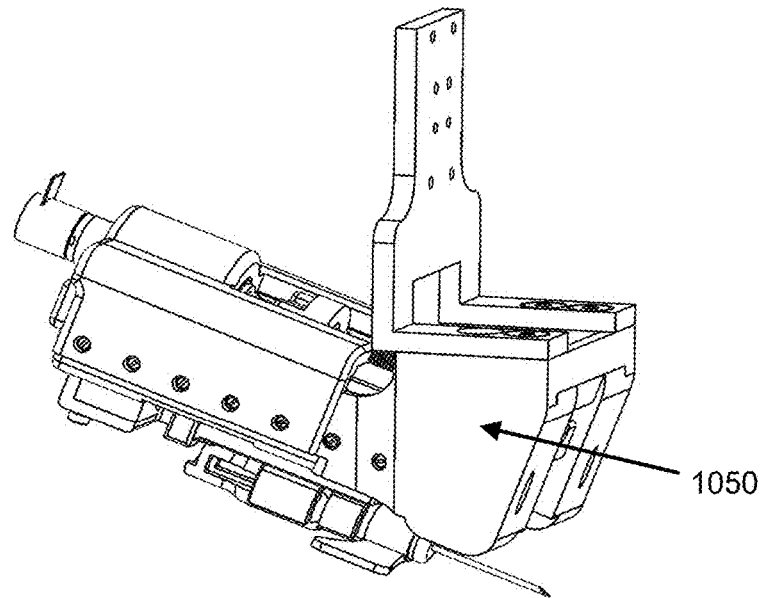

FIGS. 10C-10I provide additional views of portions of the device 1000 in order to more clearly show relation positioning of the components described in connection with FIGS. 10A and 10B. For example, FIG. 10C shows the entire device 1000, including the probe 1030 and clip 1035. FIG. 10D shows the device with the probe and clip removed, thereby more clearly showing the mounting frame 1025 to which the probe 1030 may be removably mounted. FIG. 10E shows the device with the frame and first motor removed, thereby more clearly showing the mounting frame used to mount the needle insertion housing 1050 to the rest of the manipulator. FIG. 10F shows the device with the needle housing removed, thereby more clearly showing the second motor 1040 used to drive the depth of insertion of the needle, as well as the guide rails 1070 in which the needle moves. FIG. 10G shows the device with the second motor and guide rails removed, thereby more clearly showing a housing of the bearings 1072 used to guide the needle on the guide rails. FIG. 10H shows the device with the housing removed, thereby more clearly showing the bearings 1072 and guide rails 1070, as well as a position of the electromagnet relative to the guide rails when the needle is attached, and a position of the force sensor 1064 at a back of the needle clip. Lastly, FIG. 10I shows only the force sensor, the electromagnet 1074, the needle clip 1078 and the needle 1080, as the rest of the device has been removed.

Figure 11A:
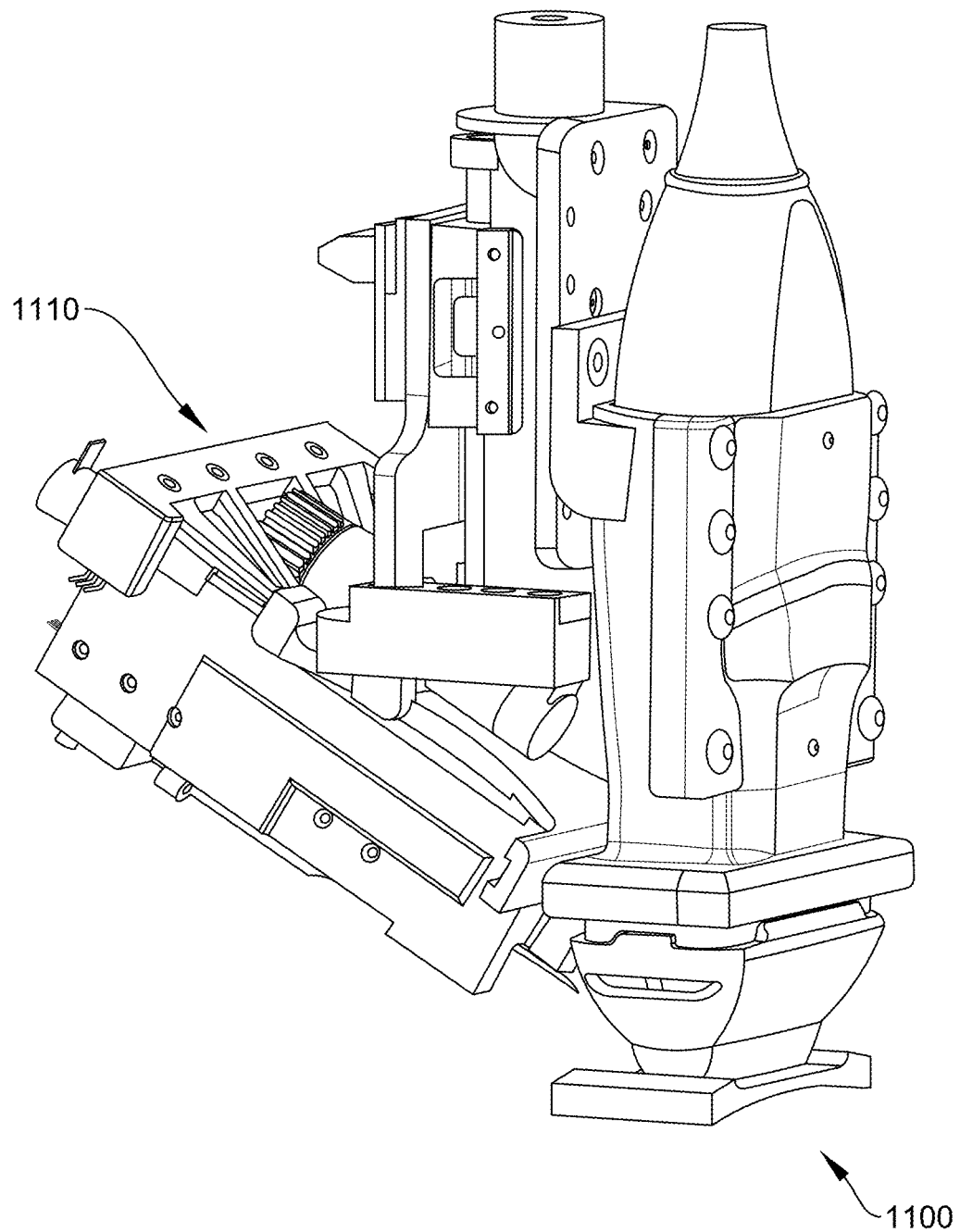
FIG. 11A is a perspective view of another cannulation device in accordance with an aspect of the present disclosure.

The example of FIGS. 10A-10I shows a structure of a device having two degrees of freedom (2-DOF). Other devices having more or fewer degrees of freedom may be designed using the example device 1000 as a base structure. For example, FIGS. 11A-11G show a device 1100 having three degrees of freedom (3-DOF). In this example, the three degrees of freedom include the same two degrees of freedom of the previous device 1000, that is, needle height and depth of insertion. Additionally, the 3-DOF device includes an additional motor for manipulating the needle in a lateral direction, along a direction of the Y-axis As shown in FIG. 11A, the device 1100 is structurally designed in a manner similar to that of the 2-DOF device 1000 described above, although not entirely the same. For example, the device 1100 still includes a probe side and a manipulator side, and the sides are mounted to one another in a similar manner. The device 1100 also has a needle insertion housing, although the housing in the 3 DOF system is somewhat larger than that of the 2 DOF system due to the presence of additional components. Some notable differences between the two structures are described in greater detail below.

Figure 11B:
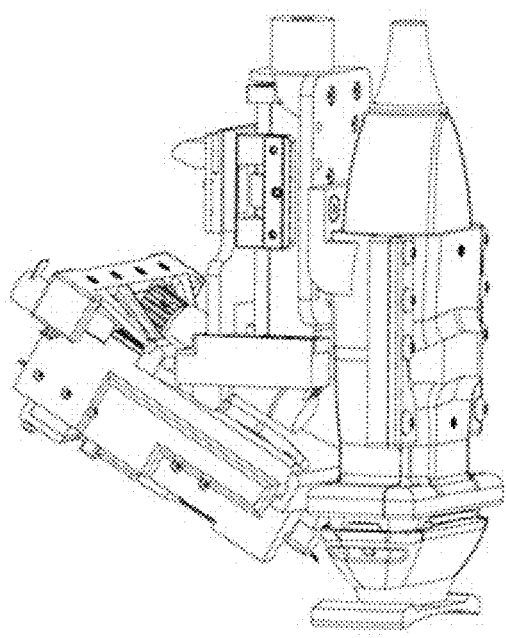
FIGS. 11B-11G are perspective views of portions of the cannulation device of FIG. 11A.
Figure 11C:
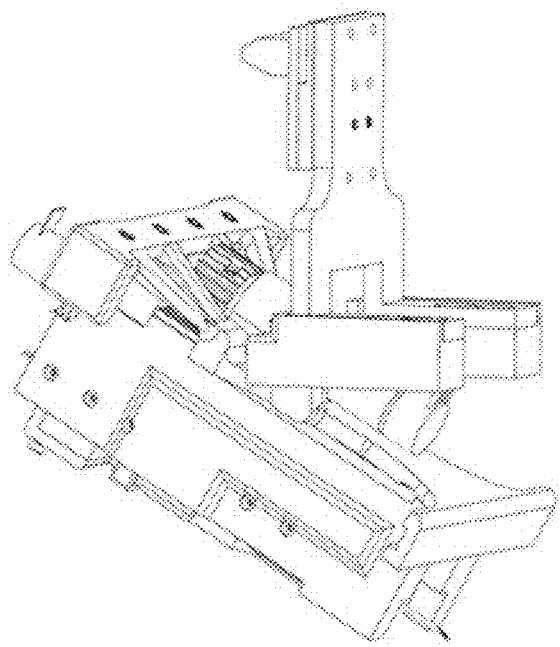
Figure 11D:
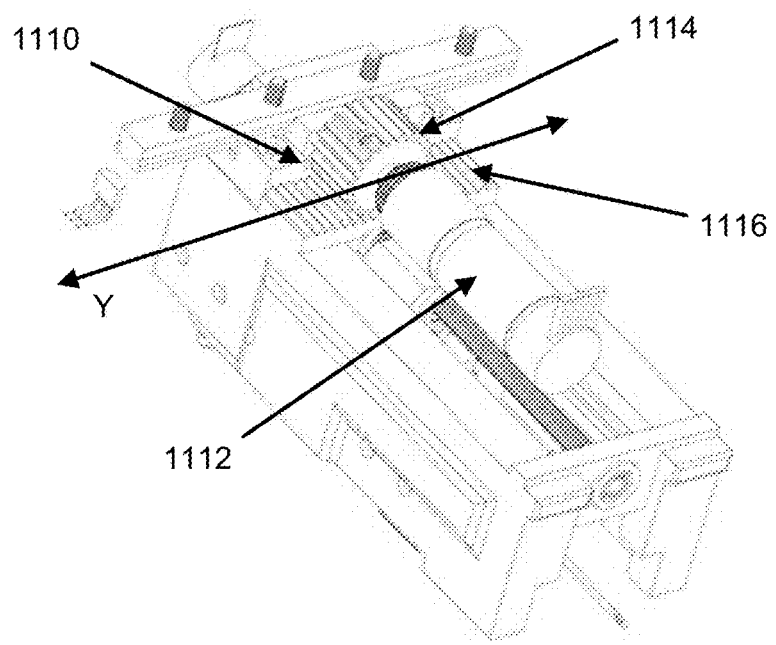

Like FIGS. 10C-10I of the 2-DOF device 1000, FIGS. 11B-11G provide additional views of portions of the 3-DOF device 1100 in order to more clearly show relation positioning of the components described in connection with FIG. 11A. FIG. 11B shows the entire device 1100, including the manipulator, probe and clip. FIG. 11C shows the device with the probe, clip, and the mounting frame for the probe removed. Also removed is the microcontroller, first motor, and their housing, in order to more clearly show the mounting frame used to mount the needle insertion housing to the rest of the manipulator. FIG. 11D shows the device with the needle housing removed, thereby more clearly showing the lateral movement mechanism 1110 used to guide the needle along the Y-axis. The lateral movement mechanism 1110 may include a third motor 1112, such as another spindle drive DC motor, used to drive a rotational motion of a gear 1114 along a track 1116. The track may have a length along the Y-axis, such that rotation of the gear 1114 causes the track 1116 to translate along the Y-axis to one side or the other. The needle clip may be coupled to the track 1116, such that translation of the track 1116 causes the needle to translate laterally as well.

Figure 11E:
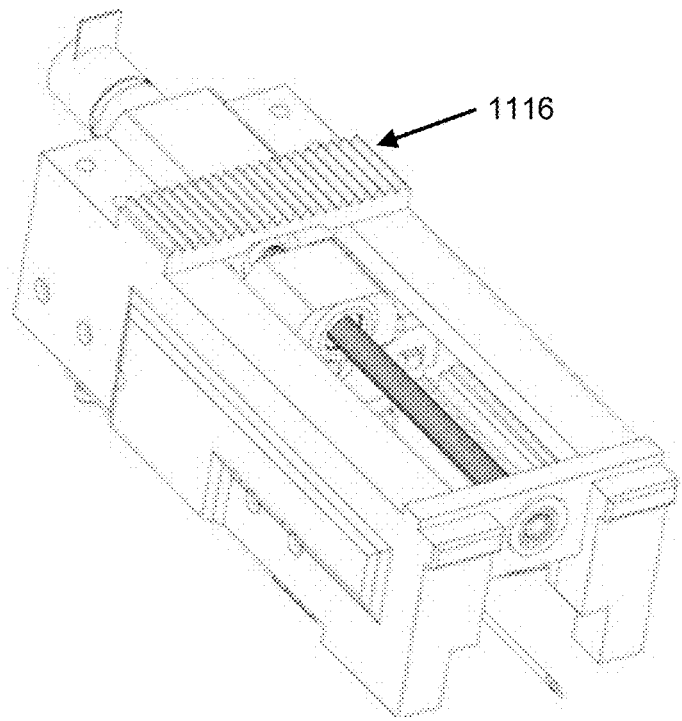
Figure 11F:
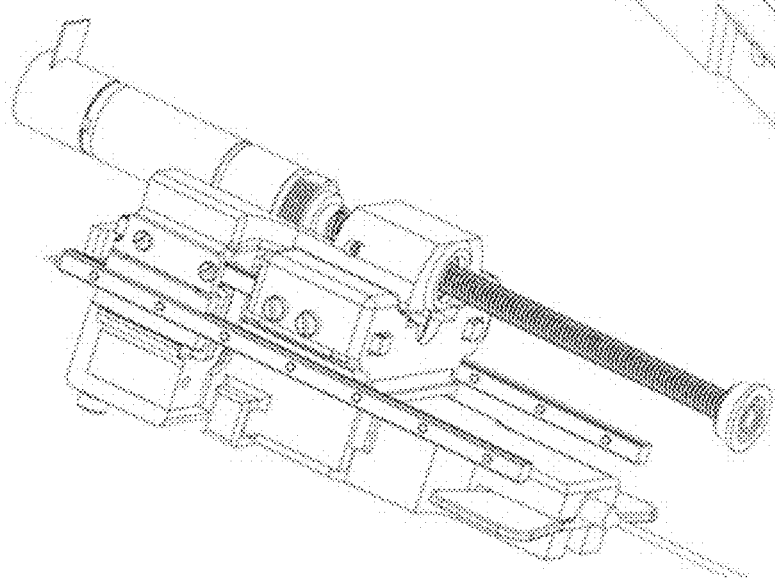
Figure 11G:
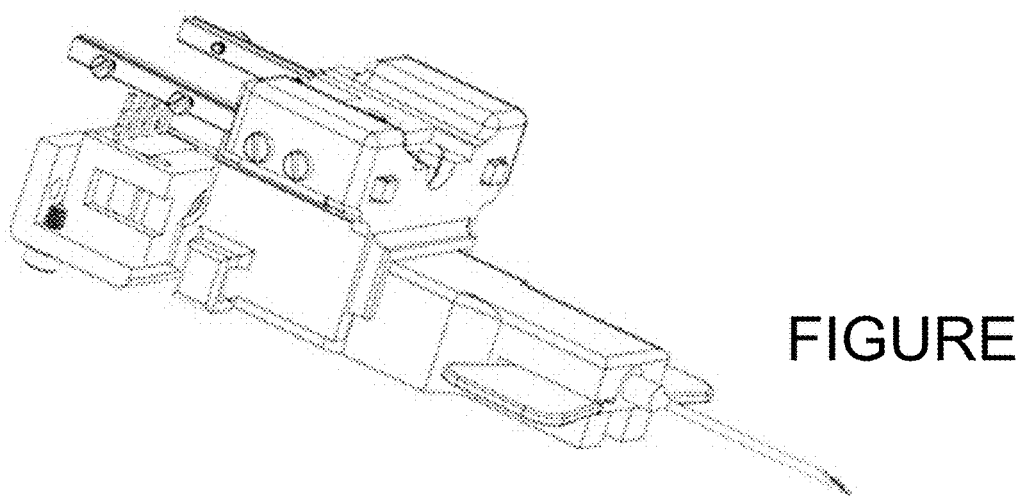

FIG. 11E shows the device with the third motor 1112 removed. The track 1116 is shown as also being coupled to the housing of the second motor, such that the second motor may be translated side to side with the needle in order to control depth of insertion independent of the needle's lateral position. FIGS. 11F and 11G are largely comparable to FIGS. 10H and 10I of the 2-DOF device 1000 described above.

Figure 12:
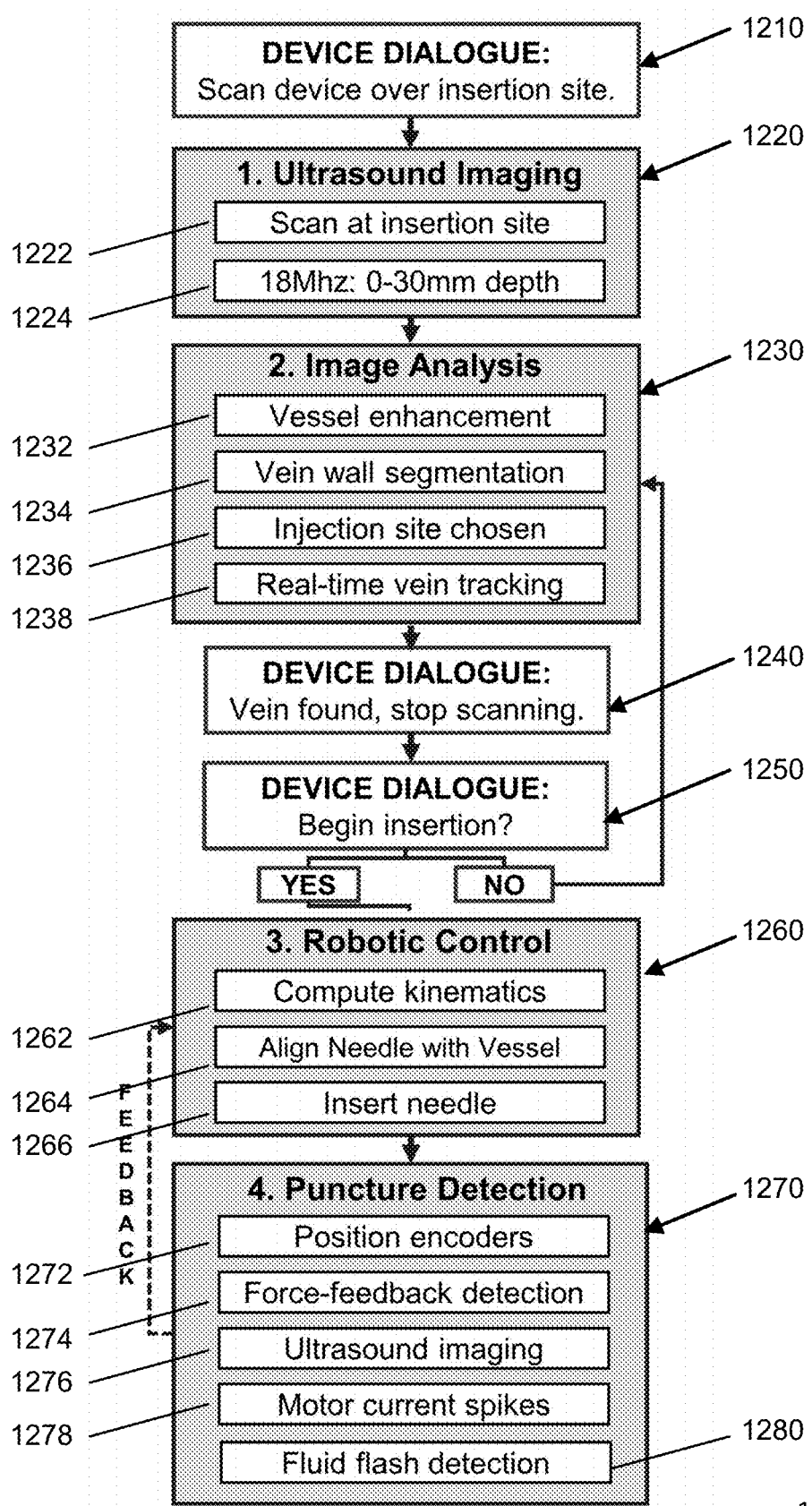
FIG. 12 is a block diagram of a workflow for operating a cannulation device in accordance with an aspect of the present disclosure.

FIG. 12 show an example workflow 1200 of a control device for controlling operation of the needle and device during a cannulation event. The workflow may begin with a scanning operation 1210, whereby the probe of the device may be positioned over the target location for cannulation. Positioning the device may include collecting image data, such as image frames from a camera or video recording device.

The workflow may continue with ultrasound imaging 1220 of the target location using the device probe. The ultrasound imaging may include an out-of-plane imaging 1222, and may provide imaging underneath the skin of the patient (e.g., 0-20 mm deep) using ultrasonic waves.

The workflow may continue with image analysis 1230 of the gathered image(s). The images may be used to identify a vessel for cannulation, and to enhance the image of the vessel 1232, such as by determining an orientation of the vessel by defining the walls of the target vessel through segmentation 1234. Ultimately, a vessel may be chosen 1236, and tracked 1238 on a frame-by-frame basis. In the case of a vein, the vein may be further analyzed to determine blood flow through the vessel to ensure that it is a good candidate for the cannulation.

Once the target vessel has been selected, the scanning may be stopped 1240 by direction of a user input. The user input may further act as a determination of whether to begin the cannulation process 1250. If it is decided not to initiate cannulation (NO), such as if the user is not satisfied with the identified target vessel, then operations may revert back to image analysis 1230 so that another target vessel may be selected. Otherwise, if insertion is to begin (YES), the workflow may continue to robotic control of the cannulation instrument 1260, which may involve computing kinematics of the free-held device if it moves above the target location 1262, aligning the cannulation instrument along the Y and Z axes in order to maintain a trajectory towards the target vessel 1264, and advancing the cannulation instrument along the depth of insertion axis towards the target vessel 1266.

When the cannulation instrument reaches the target location, the workflow may also perform a puncture detection to determine whether the instrument has been or will be properly inserted into the vessel 1270. The determination of a successful insertion may be based on several factors, including a position of the needle, such as may be indicated by the position encoders of the motors for controlling the instrument 1272, force feedback indicated by a force sensor coupled to the instrument 1274, ultrasound imaging to provide visual tracking of the insertion 1276, motor current feedback to indicate if the instrument meets an expected or unexpected resistance that would cause a spike in the motor current 1278, and blood flash or fluid flash feedback to confirm that the cannulation attempt has resulted in drawn blood or fluid 1280. Individually or collectively, this feedback data may be used in the robotic control stage 1260 of the workflow to correct instrument alignment.

The above-described devices and methods are applicable to both human patients and other animal subjects, such as in veterinary applications. More generally, those skilled in the art will readily understand and appreciate that the above-described devices methods for correcting a trajectory of a handheld cannulation instrument based on movement of a target location may be applicable to any cannulation procedure in which there can be an unexpected movement of the subject, an unexpected movement of one holding the device, or both.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A device for directing a cannula toward a target location under a patient's skin, the device comprising:
   at least one motor configured to manipulate a cannula in a lengthwise direction of the cannula towards a target location corresponding to a target vessel for cannulation,
   a set of sensors configured to:
      detect an amount of force exerted on the cannula and generate force data indicative of a force applied to the device;
      generate cannula pose data indicating a position of the cannula based on movement of the at least one motor; and
      generate a set of images that capture an under skin region extending along a length of the patient's arm; and
   a processor configured to determine whether the cannula will achieve successful insertion into the target vessel at the target location under the patient's skin by:
      receiving the force data, the cannula pose data, and the set of images from the set of sensors;
      determining a coordinate position for the target location corresponding to the target vessel based on a combination of the received force data, cannula pose data, and set of images;
      generating a trajectory to the coordinate position for the cannula; and
      monitoring the manipulation of the cannula towards the coordinate position along the generated trajectory using the set of sensors.

2. The device of claim 1, wherein the set of sensors includes one or more force sensors including a material having a property that changes in response to an applied force.

3. The device of claim 1, wherein the set of sensors includes a current sensor configured to measure an electrical current in the at least one motor, wherein electrical current in the at least one motor increases proportionally to a load on the motor.

4. The device of claim 1, wherein the at least one motor includes a plurality of motors, and wherein the set of sensors includes a plurality of motor sensors, each motor sensor associated with a corresponding one of the plurality of motors to generate the cannula pose data.

5. The device of claim 1, wherein the processor is configured to: determine an adjustment to the cannula that reduces a likelihood of failure of the successful insertion based on the combination of the received force data, cannula pose data and set of images.

6. The device of claim 1, wherein the set of images comprise two-dimensional imaging data from a plurality of angles, and wherein the processor is further configured to perform at least one of:
   constructing three-dimensional imaging data from the two-dimensional imaging data; and
   determining a three-dimensional pose for insertion into the target under the patient's skin from the two-dimensional imaging data.

7. The device of claim 1, wherein the set of sensors includes an ultrasound probe configured to generate the set of images, wherein the set of images includes imaging data generated by the ultrasound probe, and wherein the imaging data is one of: two-dimensional imaging data, volumetric three-dimensional imaging data, and biplanar imaging data.

8. The device of claim 1, wherein the processor is configured to:
   generate a force profile from force data received from the set of sensors; and
   classify the generated force profile as one of a successful cannulation event or an unsuccessful cannulation event; and
   upon occurrence of an unsuccessful cannulation event, instruct the one or more motors to manipulate the cannula in a reverse direction.

9. The device of claim 8, wherein classification of the force profile is based on a comparison of the force data against pre-stored force data profile information.

10. The device of claim 8, wherein the processor is configured to, upon occurrence of an unsuccessful cannulation event:
    classify the generated force profile as one of a vessel rolling event, an undershoot event, and an overshoot event; and
    control repositioning of the cannula according to the classified vessel rolling event, undershoot event, or overshoot event.

11. The device of claim 1, further comprising at least a second motor configured to manipulate the cannula in a second axis of movement different from the lengthwise direction.

12. The device of claim 1, wherein the at least one motor is configured to manipulate the cannula in the lengthwise direction at a predetermined speed.

13. A method for directing a cannula toward a target location under a patient's skin, the method comprising:
    manipulating, by at least one motor, a cannula in a lengthwise direction of the cannula towards a target location corresponding to a target vessel for cannulation,
    generating, by a set of sensors:
       force data indicating an amount of force exerted on the cannula;
       cannula pose data indicating a position of the cannula based on movement of the at least one motor; and
       a set of images that capture an under skin region extending along a length of the patient's arm;
    determining, by a processor, whether the cannula will achieve successful insertion into the target vessel at the target location under the patient's skin by:
       receiving, by the processor, the force data, the cannula pose data, and the set of images from the set of sensors;
       determining, by the processor, a coordinate position for the target location corresponding to the target vessel based on a combination of the received force data, cannula pose data, and set of images;

generating a trajectory to the coordinate position for the cannula; and monitoring the manipulation of the cannula towards the coordinate position along the generated trajectory using the set of sensors.

14. The method of claim 13, wherein the at least one motor includes a plurality of motors, and wherein the set of sensors includes a plurality of motor sensors, the method comprising each motor sensor generating the cannula pose data associated with a corresponding one of the plurality of motors.

15. The method of claim 13, further comprising:
determining, by the processor, an adjustment to the cannula that reduces a likelihood of failure of the successful insertion based on the combination of the received force data, cannula pose data, and set of images.

16. The method of claim 13, wherein the set of images comprise two-dimensional imaging data from a plurality of angles, the method comprising at least one of:
constructing three-dimensional imaging data from the two-dimensional imaging data; and
determining a three-dimensional pose for insertion into the target under the patient's skin from the two-dimensional imaging data.

17. The method of claim 13, wherein the set of images is generated by an ultrasound probe and includes imaging data that is one of: two-dimensional imaging data, volumetric three-dimensional imaging data, and biplanar imaging data.

18. The method of claim 13, further comprising:
generating, by the processor, a force profile from the force data received from the set of sensors;
classifying, by the processor, the generated force profile as one of a successful cannulation event or an unsuccessful cannulation event; and
upon occurrence of an unsuccessful cannulation event, instructing, by the processor, the one or more motors to manipulate the cannula in a reverse direction.

19. The method of claim 18, the method comprising, upon occurrence of an unsuccessful cannulation event:
classifying, by the processor, the generated force profile as one of a vessel rolling event, an undershoot event, and an overshoot event; and
controlling, by the processor, repositioning of the cannula according to the classified vessel rolling event, undershoot event, or overshoot event.

20. The method of claim 13, further comprising manipulating, by at least a second motor, the cannula in a second axis of movement different from the lengthwise direction.

21. The method of claim 13, manipulating, by the at least one motor, the cannula in the lengthwise direction at a predetermined speed.

* * * * *